(12) United States Patent
Berens et al.

(10) Patent No.: US 8,101,776 B2
(45) Date of Patent: Jan. 24, 2012

(54) ORGANIC SEMICONDUCTORS AND THEIR MANUFACTURE

(75) Inventors: Ulrich Berens, Binzen (DE); Frank Bienewald, Hegenheim (DE); Hans Jürg Kirner, Prattein (CA)

(73) Assignee: BASF SE, Ludwigshafen (DE)

( * ) Notice: Subject to any disclaimer, the term of this patent is extended or adjusted under 35 U.S.C. 154(b) by 677 days.

(21) Appl. No.: 12/086,157

(22) PCT Filed: Dec. 4, 2006

(86) PCT No.: PCT/EP2006/069281
§ 371 (c)(1), (2), (4) Date: Jun. 6, 2008

(87) PCT Pub. No.: WO2007/068618
PCT Pub. Date: Jun. 21, 2007

(65) Prior Publication Data
US 2009/0299070 A1    Dec. 3, 2009

(30) Foreign Application Priority Data
Dec. 12, 2005    (EP) .................................... 05111963

(51) Int. Cl.
*C07D 277/60*    (2006.01)
(52) U.S. Cl. ...................................................... 548/148
(58) Field of Classification Search .............. 549/41; 548/148
See application file for complete search history.

(56) References Cited

U.S. PATENT DOCUMENTS

| | | | |
|---|---|---|---|
| 6,252,245 B1 | 6/2001 | Katz et al. | 257/40 |
| 6,690,029 B1 | 2/2004 | Anthony et al. | 257/40 |
| 2002/0164835 A1 | 11/2002 | Dimitrakopoulos et al. | 438/99 |
| 2003/0105365 A1 | 6/2003 | Smith et al. | 568/774 |
| 2003/0144526 A1 | 7/2003 | Sakai et al. | 546/329 |
| 2006/0220007 A1 | 10/2006 | Bailey et al. | 257/40 |

FOREIGN PATENT DOCUMENTS

| | | |
|---|---|---|
| EP | 1416069 | 5/2004 |
| WO | 2005/055248 | 6/2005 |
| WO | 2005/073338 | 8/2005 |
| WO | 2006/059486 | 6/2006 |

OTHER PUBLICATIONS

King, Med Principle and Practice, (1994), pp. 206-208.*
C. Sheraw et al., Adv. Mater., vol. 15 No. 23, Dec. 3, 2003, pp. 2009-2011.
P. Lane et al., Proceedings of SPIE—The International Society for Optical Engineering; Organic Light-Emitting Materials and Devices IX, vol. 5937, (Oct. 9, 2005), pp. 1-10.
Patent Abstracts of Japan Publication No. 04164037, Jun. 9, 1992.
B. Li et al., Dyes and Pigments, vol. 62, No. 3, (Sep. 2004), pp. 299-304.
Patent Abstracts of Japan Publication No. 2002275384, Sep. 25, 2002.
M. Payne et al., Organic Letters, vol. 6, No. 19, (2004), pp. 3325-3328.
M. Payne et al., Organic Letters, vol. 6, No. 10 (2004), pp. 1609-1612.

* cited by examiner

*Primary Examiner* — Taofiq A Solola
(74) *Attorney, Agent, or Firm* — Shiela A. Loggins

(57) ABSTRACT

The invention relates to a semiconductor device comprising a compound of the formula I and of the formula XXI, wherein the symbols have the meanings defined in the specification, to the novel compounds of the formula I and XXI and to the use of such a compound as an organic semiconductor for the preparation of an electronic device, and further compounds and devices, as well as other embodiments given in the specification.

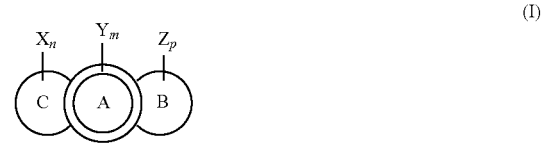

(I)

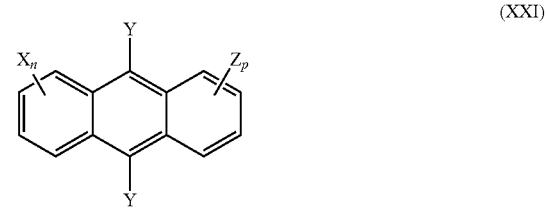

(XXI)

18 Claims, 1 Drawing Sheet

ORGANIC SEMICONDUCTORS AND THEIR MANUFACTURE

The present application pertains to a semiconductor device comprising bis(substituted ethynyl) compounds with tri- or polycyclic aromatic hydrocarbon backbones with hetero-atoms, wherein the rings that constitute the backbone (meaning the ring system formed by rings A, B and C in formula I) are annealed to each other via not more than two commonly shared ring atoms, respectively, and the number of the common atoms of the vicinal rings is twice the number of the common side areas (meaning that the rings are ortho-annealed), with the proviso that the backbone together with the (for this definition to be imagined as unsubstituted) ethynyl groups belong to certain point symmetry groups as organic semiconductor, to a process for the preparation of said devices, to the novel bis(substituted ethynyl) compounds with the backbones just defined useful inter alia in said process and devices, as well as to the use of a bis(substituted ethynyl) compound with a backbone as just defined, especially a new one, as an organic semiconductor for the preparation of an electronic device. The invention also relates to 9,10-bis-(halo-hydrocarbyl-ethynyl)-anthracenes, to a semiconductor device comprising said compounds anthracenes, process for the preparation of said compounds or devices, and the use of these anthracenes as semiconductors.

Organic semiconductor devices, e.g. organic field effect transistors (OFETs), are currently of high interest as they promise a number of advantages over traditional inorganic semiconductors, such as low-cost manufacturing or compatibility with flexible substrates. Besides certain polymers, a number of condensed aromatic compounds such as pentacene have been found to exhibit useful semiconducting properties, inter alia characterized by high charge carrier (field effect) mobility, high on/off current ratio and/or low sub-threshold voltage. These advantageous features are, however, often compromised by factors like the necessity to use vapour deposition for the preparation of thin film devices, or lack of stability due to effects like recrystallization, phase transition or oxidative/hydrolytic degradation through environmental influences.

Ideally, an organic semiconductor should be soluble in organic (or inorganic) solvents in order to be suitable for application on large areas by inexpensive methods, such as stamping, screen printing and spin-coating. Classical organic solvents, such as toluene, xylenes, chlorobenzene, o-dichlorobenzene, pyridine and the like, are appropriate solvents.

In order to improve the properties of organic semiconductors, structural modifications have been introduced into condensed aromatics, mainly in order to improve the solubility of these compounds; examples are Diels-Alder adducts which may be thermally reconverted into pentacene (US-2003-0144526), substituted pentacenes (US-2003-0105365, U.S. Pat. No. 6,690,029), tetracarboxylic acid diimides of naphthalene (U.S. Pat. No. 6,252,245) or perylene (US-2002-0164835). See also WO 05/055248.

There is a need for organic semiconductors that can provide stable, reproducible electronic performance characteristics and that exhibit good charge-carrier mobilities while allowing for low-cost manufacturing or providing the possibility for solvent processing.

It has now been found surprisingly that bis(substituted ethynyl) compounds with tri- or polycyclic aromatic hydrocarbon backbones with heteroatoms, wherein the rings that constitute the backbones are annealed to each other via not more than two commonly shared ring atoms and the number of the common atoms of the vicinal rings is twice the number of the common side areas (meaning that the rings are ortho-annealed), with the proviso that the backbone together with the (for this definition to be imagined as unsubstituted) ethynyl groups belongs to the $C_{2h}$ (preferred), $D_{2h}$ or the $C_s$ point symmetry group, can have good semiconducting properties and thus may be used as organic semiconductors in corresponding devices such as diodes, solar cells, OLEDs or especially organic field effect transistors (OFETs), which are advantageously prepared as thin film transistors (OTFTs). Apparently, the symmetry leads to especially interesting properties which may, without being bound to such an explanation, be due to good π-stacking or other properties leading to good semiconductor properties. Also surprisingly, halogenated compounds of the formula XXI shown below show good semiconductor properties.

The subject of the invention therefore generally pertains to a semiconductor device comprising a bis(substituted ethynyl) compound with a tri- or polycyclic aromatic hydrocarbon backbone with heteroatoms, wherein the rings that constitute the backbone (meaning the rings of each and any pair of annealed rings (vicinal rings) present in the whole backbone formed from rings A, B and C in formulae I or IA or the central ring in formula IB or IC and the rings therein corresponding to rings B and C, respectively; for example, if each of A, B and C in formula I is a monocyclic ring, the pairs of this kind are CA and AB) are annealed to each other via not more than two commonly shared ring atoms, respectively, (meaning the commonly shared ring atoms of each pair of rings as just defined, respectively) and the number of the common atoms of the vicinal rings (meaning the annealed rings of all ring pairs) is twice the number of the common side areas (meaning that the rings are ortho-annealed), with the proviso that the backbone together with the (for this definition to be imagined as unsubstituted) ethynyl groups belongs (i) to the $C_{2h}$ in mixture with $C_{2v}$; (ii) the $C_{2h}$; (iii) the $D_{2h}$; and/or (preferably or) (iv) the $C_s$ point symmetry group, which have the formula I (I)

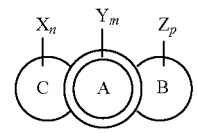

wherein the ring labelled with A is an aromatic ring with 6 atoms, the ring marked B is a mono- or polycyclic, preferably mono-, di- or tricyclic unsaturated ring or ring system or ferrocenobenzo of the subformula I(i)

(I(i))

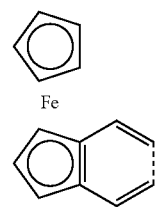

wherein the dotted bond marks the side of the benzo ring annealed to the central ring A in formula I, each annealed to ring A and the ring marked C is a mono- or polycyclic, preferably mono-, di- or tricyclic unsaturated ring or ring system or ferrocenobenzo of the subformula I(i) shown above, each annealed to ring A, each of rings or ring systems B and C may also carry a group =S, =O or =C(NQ$_2$)$_2$ (the binding double bond of which is in conjugation with the ring double bonds), where in each case where mentioned "unsaturated" means having the maximum possible number of conjugated double bonds, and wherein in at least one of rings or ring systems B and C at least one ring atom is a heteroatom selected from P, Se or preferably N, NQ, O and S, if each first ring (forming or forming part of ring or ring system B and C) directly annealed to ring A has six ring atoms;

Q is independently selected from hydrogen and (preferably) unsubstituted or substituted hydrocarbyl, unsubstituted or substituted hydrocarbylcarbonyl and unsubstituted or substituted heteroaryl;

two of the substitutents X, Y and Z (that replace hydrogen atoms that would otherwise be present at ring carbon atoms), preferably two Y substituents, are substituted ethynyl wherein the substitutents are selected from the group consisting of unsubstituted or substituted hydrocarbyl with up to 40 carbon atoms, unsubstituted or substituted hydrocarbyloxy with up to 40 carbon atoms, hydrocarbylthio with up to 40 carbon atoms, unsubstituted or substituted heteroaryl, unsubstituted or substituted heteroaryloxy, unsubstituted or substituted heteroarylthio, cyano, carbamoyl, wherein Hal represents a halogen atom, substituted amino, halo-$C_1$-$C_8$-alkyl, such as trifluoromethyl, halo, and substituted silyl;

while the remaining substituents X, Y and/or Z, as far as present, are substitutents selected from the group consisting of unsubstituted or substituted $C_1$-$C_{20}$-alkyl, such as halo-$C_1$-$C_{20}$-alkyl, unsubstituted or substituted $C_2$-$C_{20}$-alkenyl, unsubstituted or substituted $C_2$-$C_{20}$-alkynyl, unsubstituted or substituted $C_6$-$C_{14}$-aryl, especially phenyl or naphthyl, unsubstituted or substituted heteroaryl with 5 to 14 ring atoms, unsubstituted or substituted $C_6$-$C_{14}$-aryl-$C_1$-$C_{20}$-alkyl, especially phenyl- or naphthyl-$C_1$-$C_{20}$-alkyl, such as benzyl, unsubstituted or substituted heteroaryl-$C_1$-$C_{20}$-alkyl, wherein the heteroaryl has 5 to 14 ring atoms, unsubstituted or substituted ferrocenyl, unsubstituted or substituted $C_1$-$C_{20}$-alkanoyl, such as unsubstituted or perfluorinated $C_2$-$C_{12}$-alkanoyl, halo, unsubstituted or substituted $C_1$-$C_{20}$-alkoxy, $C_2$-$C_{20}$-alkenyloxy, $C_2$-$C_{20}$-alkynyloxy, unsubstituted or substituted $C_1$-$C_{20}$-alkylthio, $C_2$-$C_{20}$-alkenylthio, $C_2$-$C_{20}$-alkynylthio, carboxy, unsubstituted or substituted $C_1$-$C_{20}$-alkoxy-carbonyl, unsubstituted or substituted phenyl-$C_1$-$C_{20}$-alkoxy-carbonyl, amino, N-mono- or N,N-di-($C_1$-$C_{20}$-alkyl, $C_1$-$C_{20}$-alkanoyl and/or phenyl-$C_1$-$C_{20}$-alkyl)-amino, cyano, carbamoyl, N-mono- or N,N-di-($C_1$-$C_{20}$-alkyl, $C_1$-$C_{20}$-alkanoyl and/or phenyl-$C_1$-$C_{20}$-alkyl)-carbamoyl and sulfamoyl, and each of n and p is 0 to 4 and m is 0 to 2, with the proviso that the sum of m, n and p is at least 2 (so that at least the two substituted ethynylene groups are present); with the proviso that 5,11-bis(trialkylsilylethynyl)anthra[2,3-b:6,7-b'] dithiophene of the formula I is present in isomerically pure $C_{2h}$ form.

Figure 1:
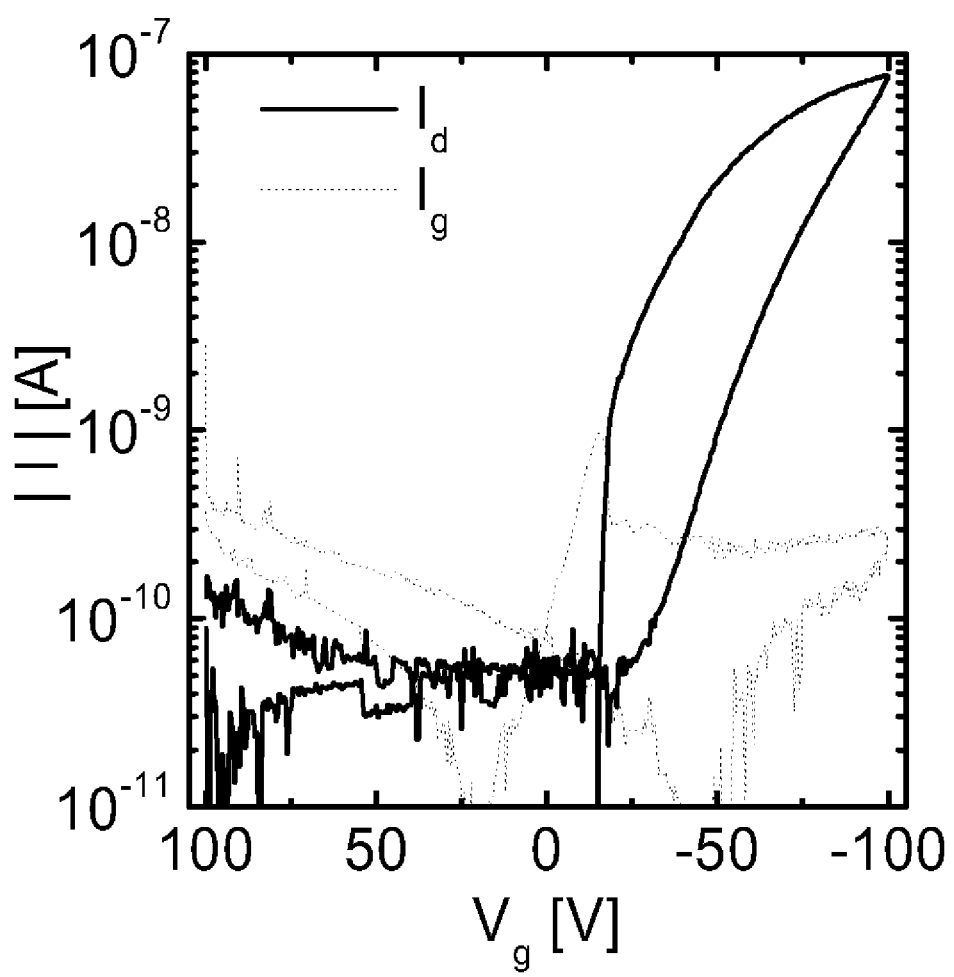
FIG. 1 shows the transfer characteristics of the thin-film device (Vg=gate voltage; Id=full line) and additionally, the gate leakage current (Ig=dotted line)

Preferably, not only the mentioned backbone but the whole molecule of the formula I (especially IA or more preferably IB or IC given below) has $C_{2h}$, $D_{2h}$ or $C_s$ point symmetry, where in the case of a molecule of the formula I, IA or IB given above or below, a compound with $C_{2h}$ point symmetry may also be present in the form of a mixture with the corresponding isomer of $C_{2v}$ symmetry (e.g. in a weight ratio from 1:5 to 5:1, preferably from 1:2 to 2:1); preferably, however, a compound of the formula I, IA or IB with $C_{2h}$ point symmetry is present in a semiconductor device in isomerically pure $C_{2h}$ form.

The bis(substituted ethynyl) compounds of the invention could also be named as [bis(substituted ethynyl)]-substituted compounds.

In one preferred embodiment, each of n and p is 0 to 4 while m is 2.

However, it is also possible that substituted ethynyl is present on rings or ring systems B and/or C as substitutent Y and/or Z, respectively, so that m can also be zero. Compounds of this type form another preferred embodiment of the invention. Examples of such compounds are those of the formulae I* or I**,

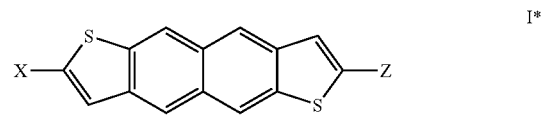

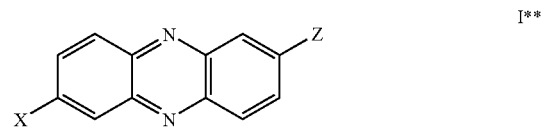

wherein X and Z are substituted ethinyl as defined for a compound of the formula I.

Preferred is a (preferably isomerically pure) bis(substituted ethynyl) compound (which is also an embodiment of the invention as such, but especially within a semiconductor device according to the invention) of the formula I according to the invention of the formula IA,

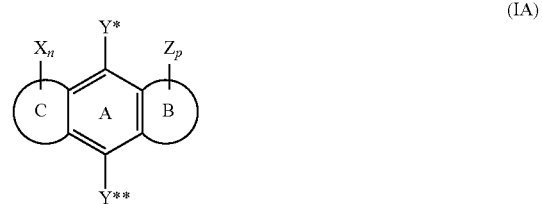

wherein

X, Z, and the rings marked A, B and C, n and p are as defined for a compound of the formula I and Y* and Y** are independently selected from substituted ethynyl as defined above or preferably below, which compounds also fulfil the point group and ring binding criteria given above for compounds of the formula I, with the proviso that 5,11-bis(tri-alkylsilyl-ethynyl)anthra[2,3-b:6,7-b']dithiophene of the formula I is present in isomerically pure $C_{2h}$ form.

Yet more preferred (preferably isomerically pure) bis(ethynyl)substituted ethynyl compounds of the formula I according to the invention are compounds of the formula IB,

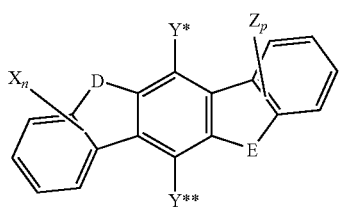

(IB)

wherein each of D and E is a heteroatom independently selected from the group consisting of O, NQ or S; X, Z, n and p are as defined for a compound of the formula I; and Y* and Y** are independently selected from substituted ethynyl, which compounds also fulfil the point group and ring binding criteria given above for compounds of the formula I.

Also yet more preferred (preferably isomerically pure) bis(ethynyl)substituted ethynyl compounds of the formula I according to the invention are compounds of the formula IC,

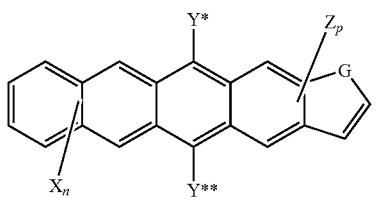

(IC)

wherein G is a heteroatom selected from the group consisting of O, NQ or S, X, Z, n and p are as defined for a compound of the formula I; and Y* and Y** are independently selected from substituted ethynyl, which compounds also fulfil the point group and ring binding criteria given above for compounds of the formula I.

The compounds useful or according to the present invention have at least a tri-cyclic backbone (meaning that three rings A, B and C in formula I and IA are present), but they also can comprise more rings and thus be polycyclic, e.g. with up to 12, preferably up to 8, more preferably up to 5 annealed rings, e.g. as shown in compounds of the formula IB or IC.

The rings are annealed to each other via not more than two carbon atoms per ring pair that contributes to the backbone of the compounds of the formula I, IA, IB or IC so that the total number of the common atoms of all the vicinal ring pairs is twice the number of the common side areas (such side areas are indicated by the tips of the arrows in formula (AA) and formula (BB) below, the common ring atoms by the letter R). This means that all the rings are ortho-annealed, as for example illustrated (without meaning that this is a preferred variant) in a compound of formula (AA)

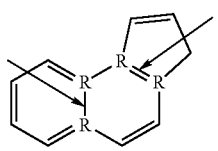

(AA)

and not via three or more common ring atoms as in a compound of the formula (BB) (here the number of common side areas is less than the double of the number of common ring atoms).

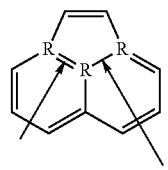

(BB)

Where a substituted ethynyl group is mentioned, this is intended to mean a group of the subformula —C≡C-Ya, wherein Ya is a substitutent as mentioned above or below for substituted ethynyl.

Where, in the definition of the point group of the backbone, "unsubstituted ethynyl" is referred to, this is intended to mean a group of the subformula "—C≡C—H".

The proviso that the backbone together with the (for this definition to be imagined as unsubstituted) ethynyl groups belongs to the $C_{2h}$ (preferred) or the $D_{2h}$ point symmetry group means the following:

A point symmetry of the class $C_{2h}$ (which is the most preferred symmetry of the backbone (meaning the ring system formed from rings A, B and C in formula I, from B and C and the central ring in formulae IA and IB) of the molecule, preferably of the whole molecule of the formulae I, IA or IB, together with the (for this definition to be imagined as unsubstituted) ethynyl groups and preferably of the whole molecule of the formula I) means that one two-fold axis of rotation is present and a mirror plane, to which the axis of rotation is vertical. For example, the following molecule shows this type of symmetry (the circular arrow in the center of the molecule indicating the rotation around the diadic central axis, while the plane of symmetry is in the plane of the page):

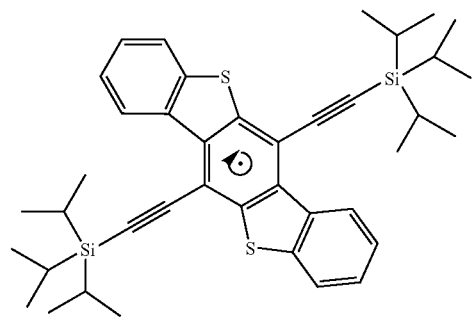

A point symmetry of the class $D_{2h}$ (which is another very preferred symmetry of the backbone (meaning the ring system formed from rings A, B and C in formula I, from B and C and the central ring in formulae IA and IB) of the molecule, preferably of the whole molecule of the formulae I, IA or IB, together with the (for this definition to be imagined as unsubstituted) ethynyl groups and preferably of the whole molecule of the formula I) means that one two-fold axis of rotation as main axis, two-fold axis of rotation, 2 mirror planes that include the main axis and one plane perpendicular to the main axis are present. For example, the following molecule shows this type of symmetry:

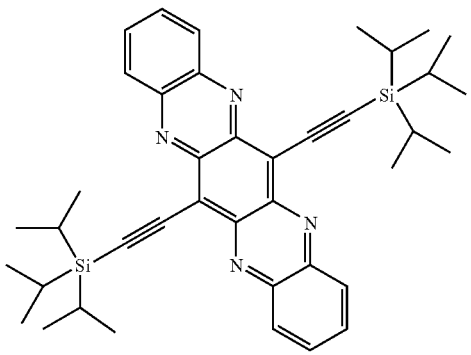

A point symmetry of the class $C_s$ (which is yet another very preferred symmetry of the backbone (meaning the ring system formed from rings A, B and C in formula I, from B and C and the central ring in formulae IA and IC) of the molecule, preferably of the whole molecule of the formulae I, IA or IC, together with the (for this definition to be imagined as unsubstituted) ethynyl groups and preferably of the whole molecule of the formula I) means only one mirror plane is present, as for example in the following molecule:

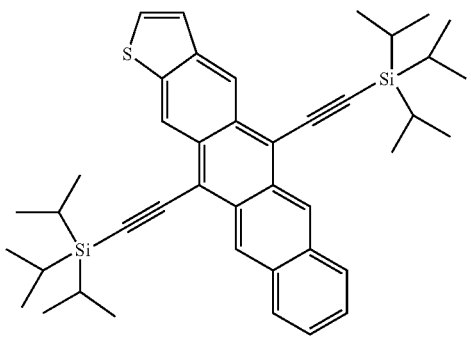

A point symmetry of the class $C_{2v}$ means a molecule that has one two-fold axis of rotation and two perpendicular mirror planes containing the two-fold axis of rotation (that is, the planes are parallel to the axis of rotation).

Any one of the compounds of formula I (with symbols as defined for formula I, preferably as defined as preferred), a semiconductor device comprising it or its use in a semiconductor mentioned in the following forms an especially preferred embodiment of the invention:

In the case of a molecule of the formula I, IA or IB given above or below, a compound with $C_{2h}$ point symmetry is present in the form of a mixture with the corresponding isomer of $C_{2v}$ symmetry (e.g. in a weight ration from 1:5 to 5:1, preferably from 1:2 to 2:1), except for 5,11-bis(trialkylsilylethynyl)anthra[2,3-b:6,7-b']dithiophene of the formula I which is present in isomerically pure $C_{2h}$ form;

preferred is a compound of the formula I, IA, IB or IC in isomerically pure form.

More preferred is a compound of the formula I with $C_{2h}$ symmetry, either in mixture with a corresponding compound of $C_{2v}$ point symmetry, except for 5,11-bis(trialkylsilylethynyl)-anthra[2,3-b:6,7-b']dithiophene of the formula I which is isomerically pure or preferably in isomerically pure form;

a compound of the formula I with $D_{2h}$ symmetry; or a compound of the formula I with $C_s$ symmetry.

That a molecule in accordance with the invention is present in (essentially) isomerically pure form or is isomerically pure means that the isomeric purity, preferably with regard to constitution isomerism, more preferably with regard to both constitution isomerism and stereoisomerism, most preferably regarding point symmetry, of the compound of the formula I (preferably of formula IA, more preferably of formula IB or IC) as such is preferably 75% or higher related to other isomers of the same molecule, more preferably 90% or higher, yet more preferably 95% or higher and most preferably 98% or higher. Other components (such as electrodes, substrates and the like) of semiconductor devices according to the present invention will, of course, comprise other materials, the essential purity merely relating to a compound of the formula I present in such device in a specific compartment (e.g. a film layer) of said device. Where more than one semiconducting components with a compound of the formula I are present in such a semiconductor device, e.g. in different layers, they may comprise different compounds of the formula I, e.g. with different conductivity properties or the like.

Generally, that 5,11-bis(trialkylsilylethynyl)anthra[2,3-b:6,7-b']dithiophene is present in isomerically pure $C_{2h}$ form means that the compound does not comprise more than 25, more preferably not more than 10%, yet more preferably not more than 5%, still more preferably 2% or less, most preferably 0.5% or less of the isomer with $C_{2v}$ symmetry (5,11-bis-(trialkylsilylethynyl)anthra[2,3-b:7,6-b']dithiophene) as "impurity". Where the corresponding proviso is mentioned, this means that the compound (as such, in a semiconductor device or for the manufacture thereof) is present in the isomerically pure $C_{2h}$ form, with little or practically no $C_{2v}$ isomer as impurity (as given in the immediately preceding sentence).

Where reference is made in the preceding and following text (description and/or claims) to a compound of the formula I, a compound of the formula IA, a compound of the formula IB or a compound of the formula IC this is meant preferably to include only such compounds that fulfil the purity, point (symmetry) group and type of annealing of rings conditions as set forth above or below.

Ring A in a compound of the formula I is an aromatic ring with 6 atoms which has either only ring carbon atoms (preferred, see formula IA) or comprises one or more, e.g. up to two N heteroatoms instead of carbon atoms and with the maximum number of conjugated double bonds possible, preferably a benzene ring annealed to rings or ring systems B and C.

The ring marked B in formula I or IA is a mono- or polycyclic, preferably mono- or dicyclic unsaturated ring or ring system annealed to ring A via two common ring atoms, which carries the maximum possible number of conjugated double bonds and in which instead of a ring carbon atom preferably (but not necessarily) at least one heteroatom is present. Preferably, the mono- or polycyclic ring or ring system has (including the ring atoms via which it is annealed to ring A) 4 to 20, more preferably up to 14 ring atoms. The heteroatom or heteroatoms if present are selected from P, Se or preferably O, S, and N or NQ, where Q is as defined for a compound of the formula I.

The ring or ring system marked C in formula I or IA is a mono- or polycyclic, preferably mono- or dicyclic unsaturated ring or ring system annealed to ring A via two common ring atoms, which carries the maximum possible number of conjugated double bonds and in which at least one heteroatom is present. Preferably, the mono- or polycyclic ring or ring system has (including the ring atoms via which it is annealed to ring A) 4 to 20, more preferably up to 14 ring atoms. The heteroatom or heteroatoms are selected from P, Se or preferably O, S, and N or NQ, where Q is as defined for a compound of the formula I. Preferred rings may be those mentioned above for the ring marked A in formula I or IA.

The condition "if the first ring forming or forming part of ring or ring system B and C directly annealed to ring A has six ring atoms in both rings or ring systems B and C" means that at least one hetero ring atom as mentioned is present in at least one of the rings or ring systems B or C, if both rings of B and C, which are directly annealed (i.e. fused) to ring A, have 6 ring atoms. In case that B and/or C comprise two or more rings, this ring or these rings having 6 ring atoms are those part(s) of B and/or C directly annealed to ring A. If, in contrast, at least one of these rings annealed to A has seven or preferably five ring atoms, B and C may be purely carbocyclic (i.e. $CQ_2$ may be present instead of a heteroatom). Preferred are compounds wherein B and/or C contain a hetero ring atom.

Examples of preferred mono- or polycyclic rings B and C are (where the side of the respective ring system with the dotted bond represents the side of the ring common with ring A and the point group class if given below the formulae is only a preferred point group class where rings B and C are identical and bonded to two opposite sides of the central ring A which thus relates to preferred embodiments, and where each of these mono- or polycyclic rings may be unsubstituted or substituted as defined below):

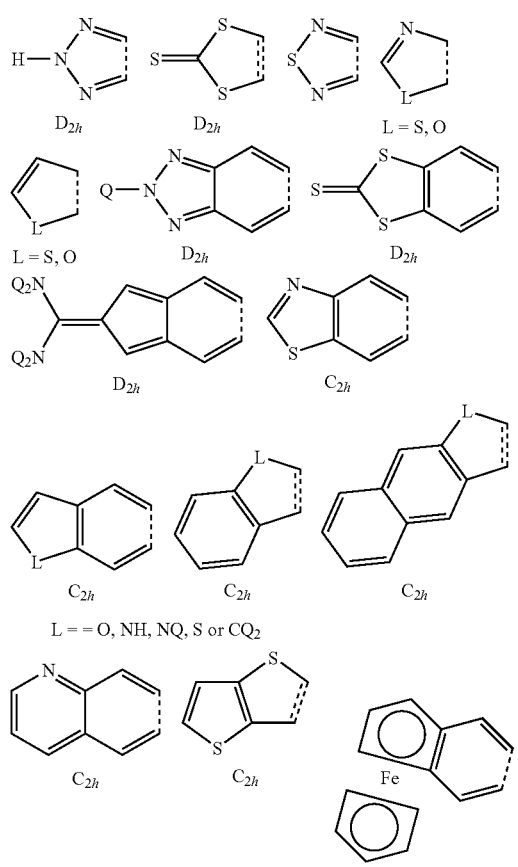

(the latter representing ferrocenobenzo in the nomenclature of the present disclosure).

Further, provided that ring C has at least one heteroatom, it is possible that ring B can also be of the formula

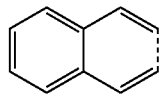

(the dotted line again representing the side annealed to the rest of the molecule).

Where Q is mentioned, this for each occurrence of Q and each ring independently of the other relates to hydrogen or an unsubstituted or substituted hydrocarbyl, unsubstituted or substituted hydrocarbylcarbonyl or unsubstituted or substituted heteroaryl as defined above or below for X or Z; preferably, Q is selected from hydrogen, aryl, especially $C_6$-$C_{14}$-aryl, aryl-alkyl, especially phenyl- or naphthyl-$C_1$-$C_{20}$-alkyl, and alkyl, especially $C_1$-$C_{20}$-alkyl, heteroaryl, especially the radical of a mono-, bi- or tricyclic ring system with 5 to 14 ring atoms and with up to three heteroatoms selected from N, O and S, and haloalkyl, especially perfluoro-$C_1$-$C_{20}$-alkyl. Where more than one moiety Q is present, each can be equal to or different from the others. The rings or ring systems B and C can be unsubstituted or substituted by one or more, preferably up to three independently selected substitutents selected from those mentioned below as substituents for "substituted moieties".

The rings marked B and C in formula I or formula IA can be the same (preferred, especially leading to $C_{2h}$ or $D_{2h}$ point symmetry) or different (e.g. for the case of $C_s$ symmetry).

In each case where mentioned "unsaturated" means having the maximum possible number of conjugated double bonds.

Substituted ethynyl is ethynyl (—C≡C—H) wherein the hydrogen is substituted by one of the substitutents mentioned above, where general expression can preferably be replaced by the more detailed definitions given below.

$C_1$-$C_{40}$-hydrocarbyl (also in $C_1$-$C_{40}$-hydrocarbyl-thio, hydrocarbyloxy or ($C_1$-$C_{40}$-) hydrocarbylcarbonyl (=hydrocarbyl-C(=O)—)) preferably means a moiety with 1 to 40 carbon atoms which (i) may be (fully) unsaturated, partially saturated (e.g. comprising one or more double and/or triple bonds where possible) or fully saturated, may (ii) be linear, branched, mono- or poly- (e.g. mono-, di- or tri)-cyclic or a combination thereof and is bound via a carbon or via a carbon carrying an oxo group; especially selected from an unsubstituted or substituted moiety selected from the group consisting of $C_1$-$C_{40}$-alkyl (preferably $C_1$-$C_{20}$-alkyl),
$C_2$-$C_{40}$-alkenyl (preferably $C_2$-$C_{20}$-alkenyl),
$C_2$-$C_{40}$-alkinyl (preferably $C_2$-$C_{20}$-alkinyl),
$C_4$-$C_{40}$-alkyldienyl,
$C_6$-$C_{20}$-aryl (preferably $C_6$-$C_{14}$-aryl),
$C_7$-$C_{40}$-(mono, di or tri-alkyl)-aryl,
$C_7$-$C_{40}$-arylalkyl $C_3$-$C_{40}$-cycloalkyl,
$C_3$-$C_{40}$-cycloalkenyl,
ferrocenyl,
or the like.

Where in the present disclosure substituted moieties, e.g. for substituted hydrocarbyl, hydrocarbyloxy or heteroaryl, are mentioned, and if not defined otherwise (e.g. as in the following two paragraphs), one or more, especially up to five selected independently from each other can be present, or in the case of fluorine up to all of the H atoms of the corresponding moiety can be replaced with fluorine (e.g. in the case of perfluorinated alkyl), and the substitutents, as well as in the case where "general substituent definitions" are mentioned above or below, are preferably selected from the group consisting of substituted silyl* as defined below, formyl, $C_1$-$C_{20}$-alkyl*, $C_2$-$C_{20}$-alkenyl*, $C_2$-$C_{20}$-alkinyl*, $C_6$-$C_{14}$-aryl*, especially phenyl* or naphthyl*, $C_6$-$C_{14}$-aryl-$C_1$-$C_{20}$-alkyl*, especially phenyl- or naphthyl-$C_1$-$C_{20}$-alkyl*, heteroaryl with 5 to 14 ring atoms*, heteroaryl-$C_1$-$C_{20}$-alkyl* wherein heteroaryl has 5 to 14 ring atoms, halo-$C_1$-$C_{20}$-alkyl*, e.g. perfluorinated $C_1$-$C_{20}$-alkyl, $C_1$-$C_{20}$-alkanoyl*, halo-$C_1$-$C_{20}$-alkylcarbonyl (=$C_1$-$C_{20}$—C(=O)—), e.g. perfluorinated $C_1$-$C_{20}$-alkylcarbonyl, halo, hydroxy, SH, $C_1$-$C_{20}$-alkoxy, $C_2$-$C_{20}$-alkenyloxy, $C_2$-$C_{20}$-alkynyloxy, $C_1$-$C_{20}$-alkthio, $C_2$-$C_{20}$-alkenylthio, $C_2$-$C_{20}$-alkynylthio, carboxy, $C_1$-$C_{20}$-alkoxy-carbonyl*, phenyl-$C_1$-$C_{20}$-alkoxy-carbonyl*), amino (less preferred), N-mono- or N,N-di-($C_1$-$C_{20}$-alkyl, $C_1$-$C_{20}$-alkanoyl, naphthyl-$C_1$-$C_{20}$-alkyl and/or phenyl-$C_1$-$C_{20}$-alkyl)-amino; cyano, carbamoyl, N-mono- or N,N-di-($C_1$-$C_{20}$-alkyl, $C_1$-$C_{20}$-alkanoyl, naphthyl-$C_1$-$C_{20}$-alkyl and/or phenyl-$C_1$-$C_7$-alkyl)-carbamoyl, nitro and sulfamoyl, where the substituents marked with an asterisk (*) can also be bound to a nitrogen instead of an H, e.g. substituting a ring NH in a heterocycle.

Wherever $C_1$-$C_{20}$—, $C_2$-$C_{20}$— or $C_3$-$C_{20}$— is used, this can preferably relate to $C_1$-$C_8$—, $C_2$-$C_8$— or $C_3$-$C_8$—, respectively, or to $C_8$-$C_{20}$—.

In the case of substituted amino, the substituents are preferably selected from unsubstituted or substituted hydrocarbyl, each with up to 40 carbon atoms, as mentioned above, from unsubstituted or substituted hydrocarbylcarbonyl (hydrocarbyl-C(=O)—) with up to 40 carbon atoms in addition to the carbonyl carbon, from unsubstituted or substituted heteroaryl or from unsubstituted or substituted heteroarylcarbonyl.

Substituted silyl is preferably Si substituted by two or preferably three moieties selected from unsubstituted or substituted hydrocarbyl or hydrocarbyloxy (wherein the substituents are preferably other than substituted silyl), as defined above, or by unsubstituted or substituted heteroaryl. In case that Si carries only two substituents, the silyl group is of the type —SiH($R_2$) with R preferably being hydrocarbyl. More preferred are three $C_1$-$C_{20}$-alkyl or -alkoxy substituents, especially three $C_1$-$C_8$-alkyl substitutents, such as methyl, ethyl, isopropyl, t-butyl or isobutyl.

Carbamoyl usually stands for a residue —CO—$NQ_2$; sulfamoyl, similarly, for a residue —S($O_2$)—$NQ_2$.

As substituted ethynyl, ethynyl substituted by unsubstituted or substituted $C_1$-$C_{20}$-alkyl (which can be primary, secondary or tertiary), unsubstituted or substituted phenyl, unsubstituted or substituted (e.g. 1- or 2-) naphthyl, unsubstituted or substituted (e.g. 1-, 2- or 9-) anthracenyl, an unsubstituted or substituted heteraryl moiety or a substituted silyl moiety selected from those given in the following table—the respective moiety can be bound via any ring atom appropriate, preferably by one of those marked with an asterisk, to the ethynyl moiety instead of a hydrogen in unsubstituted ethynyl—are especially preferred:

Table of some preferred substitutents for substituted ethynyl (which can be substituted or preferably unsubstituted as described above):

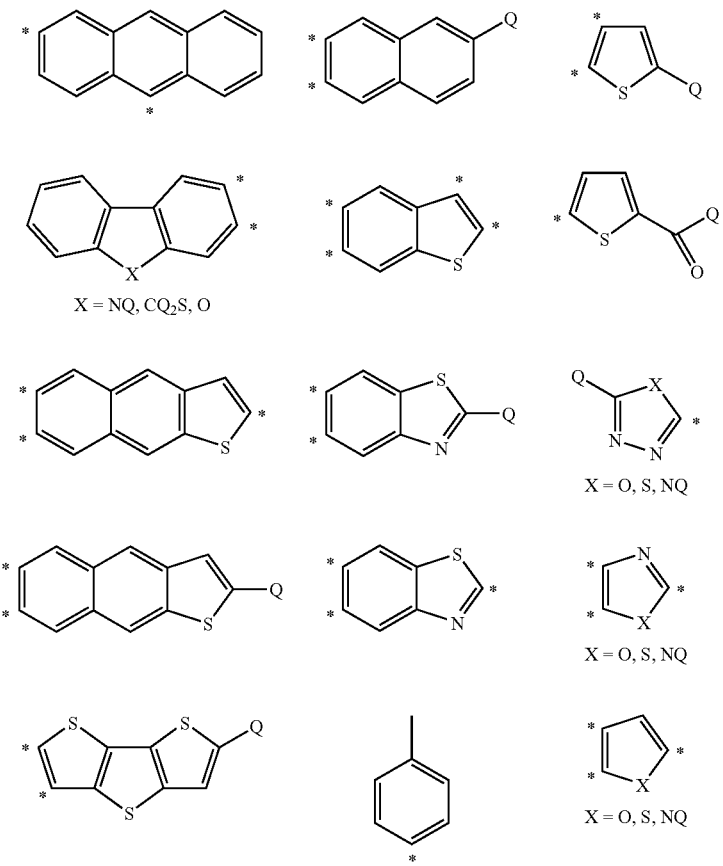

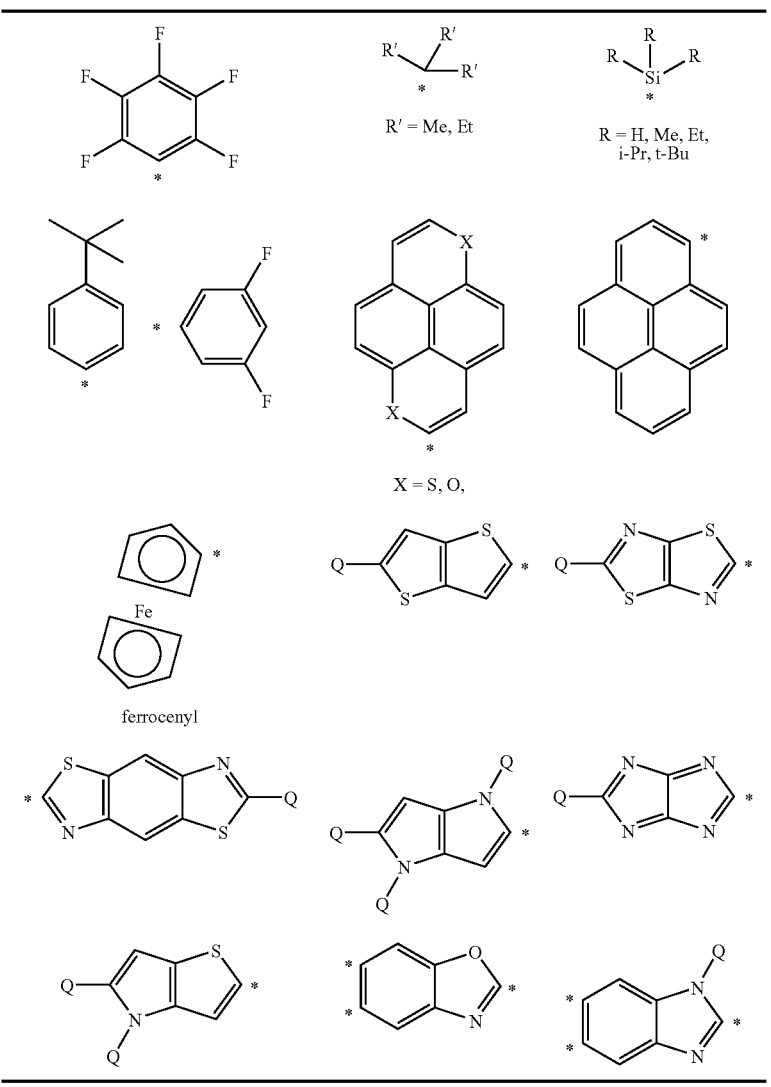

In the table, Q is as defined above for a compound of the formula I, especially selected from hydrogen, aryl, especially $C_6$-$C_{14}$-aryl, aryl-alkyl, especially phenyl- or naphthyl-$C_1$-$C_{20}$-alkyl, heteroaryl, especially with up to 14 ring atoms, and alkyl, especially $C_1$-$C_{20}$-alkyl.

Generally, binders and/or dotants or the like may be present in a semiconductor device according to the present invention, however, preferably in an amount of less than 5%, e.g. in thin films in thin film transistors which are described in more detail below. Possible binders are, e.g., described in WO 2005/055248 which is incorporated here by reference concerning the binders and compositions where the polyacenes of formula A therein are replaced with compounds of the formula I, preferably IA and more preferably IB or IC as described in the present text.

The alkyl, alkenyl or alkynyl moieties mentioned herein can be linear or branched one or more times (if the number of carbon atoms therein allows so). Preferably, they have up to 20 carbon atoms, in another preferred embodiment up to 8 carbon atoms.

The term alkyl, wherever used, thus mainly embraces especially $C_1$-$C_{20}$alkyl such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Alkoxy is alkyl-O—, alkylthio is alkyl-S—).

Where aryl (e.g. in $C_1$-$C_{14}$-aryl) is used, this preferably comprises monocyclic rings or polycyclic ring systems with the highest possible number of double bonds, such as preferably phenyl, naphthyl, anthrachinyl, anthracenyl or fluorenyl.

Heteroaryl is preferably a mono- or polycyclic, e.g. mono-, di- or tricyclic, ring or ring system with one or more, e.g. one to three, hetero ring atoms selected from P, Se, or preferably N, NQ, O and S, up to 20 ring atoms, e.g. 5 to 14 ring atoms, that can be unsubstituted or substituted as described above, with Q as defined below. Examples for heteroaryl (which can be unsubstituted or substituted as described above) include those of the following table:

| Ring Structure | Name | Monovalent Heteroaryl Residue |
|---|---|---|
| | pyridine | pyridyl |
| | pyrimidine | pyrimidyl |
| | pyridazine | pyridazyl |
| | pyrazine | pyrazyl |
| | thiophene | thienyl |
| | benzothiophene | benzothienyl |
| | pyrrol | pyrryl |
| | furane | furyl |
| | benzofurane | benzofuryl, |
| | indole | indolyl |
| | carbazole | carbazolyl |
| | benzotriazole | benzotriazolyl |
| | tetrazole | tetrazolyl |
| | thiazole | thiazolyl | which are bonded via a carbon ring atom,
or a moiety selected from the following moieties (bonded preferably via one of the carbon atoms labelled with an asterisk):

thienothienyl dithiaindacenyl chinolyl isochinolyl chinoxalyl acridyl wherein Q has one of its meanings other than hydrogen benzo[1,2-d;4,5-d']bisthiazolyl carbazolyl wherein Q has one of its meanings other than H;

dibenzothiophenyl wherein Q has one of its meanings other than hydrogen;

thiazolo[5,4-d]thiazolyl as well as phenanthrolyl, triazinyl, thienyl, pyrazolyl, imidazolyl, or thia- and oxadiazolyl $(=$ [structure] $X = O, S.)$ Halogen (if not mentioned otherwise) denotes I, Br, Cl, F, preferably Cl, F, especially F. Halo thus denotes a halogen substituent. Where haloalkyl or the like is mentioned, one or more halogen substituents can be present, e.g. in trifluoromethyl.

The invention also relates to a compound of the formula XXI,

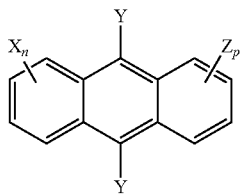

wherein each Y, independently of the other, is ethynyl substituted by halo-substituted hydrocarbyl with up to 40 carbon atoms or by heteroaryl;

X and Z, independently from each other, (if present) are substitutents selected from the group consisting of unsubstituted or substituted $C_1$-$C_{20}$-alkyl, such as halo-$C_1$-$C_{20}$-alkyl, unsubstituted or substituted $C_2$-$C_{20}$-alkenyl, unsubstituted or substituted $C_2$-$C_{20}$-alkynyl, unsubstituted or substituted $C_6$-$C_{14}$-aryl, especially phenyl or naphthyl, unsubstituted or substituted heteroaryl with 5 to 14 ring atoms, unsubstituted or substituted $C_6$-$C_{14}$-aryl-$C_1$-$C_{20}$-alkyl, especially phenyl- or naphthyl-$C_1$-$C_{20}$-alkyl, such as benzyl, unsubstituted or substituted heteroaryl-$C_1$-$C_{20}$-alkyl, wherein the heteroaryl has 5 to 14 ring atoms, unsubstituted or substituted ferrocenyl, unsubstituted or substituted $C_1$-$C_{20}$-alkanoyl, such as unsubstituted or perfluorinated $C_2$-$C_{12}$-alkanoyl, halo, unsubstituted or substituted $C_1$-$C_{20}$-alkoxy, $C_2$-$C_{20}$-alkenyloxy, $C_2$-$C_{20}$-alkynyloxy, unsubstituted or substituted $C_1$-$C_{20}$-alkylthio, $C_2$-$C_{20}$-alkenylthio, $C_2$-$C_{20}$-alkynylthio, carboxy, unsubstituted or substituted $C_1$-$C_{20}$-alkoxy-carbonyl, unsubstituted or substituted phenyl-$C_1$-$C_{20}$-alkoxy-carbonyl, amino, N-mono- or N,N-di-($C_1$-$C_{20}$-alkyl, $C_1$-$C_{20}$-alkanoyl and/or phenyl-$C_1$-$C_{20}$-alkyl)-amino, cyano, carbamoyl, N-mono- or N,N-di-($C_1$-$C_{20}$-alkyl, $C_1$-$C_{20}$-alkanoyl and/or phenyl-$C_1$-$C_{20}$-alkyl)-carbamoyl and sulfamoyl, and each of n and p, independently of the other, is 0 to 4, preferably 0 or 1.

The invention also relates to a semiconductor device comprising a compound of the formula XXI, a process for the manufacture of a compound of the formula XXI, a process for the manufacture of a semiconductor device comprising using a compound of the formula XXI and the use of a compound of the formula I as semiconductor.

Hydrocarbyl and heteroaryl are preferably as defined above for a compound of the formula I, more preferably hydrocarbyl is $C_6$-$C_{14}$-aryl, such as phenyl, naphthyl or 9-fluorenyl. Halo-substituted means that the hydrocarbyl moiety carries one or more halogen atoms, such as chloro or bromo. Highly preferred are compounds of the formula I wherein Y is 4-halophenyl, such as 4-chloro- or 4-bromophenyl.

Very preferred is a semiconductor device comprising a compound of the formula I or a compound of the formula XXI as given in the examples, as well as a compound of the formula I or of the formula XXI as described in the examples; or the use thereof in the manufacture of a semiconductor device.

The novel compounds of the formula IA and especially of the formula IB or IC, including those of the formula I*, I and I*, as well as those of the formula XXI, of the invention are in addition to the utilities mentioned above and below also useful as fluorescent dyes or as light, especially infrared, absorbing materials, or solar cells.

Where compounds of the formula I are mentioned herein, those of the formula IA and especially those of the formula IB or IC are preferred.

Where more general expressions or symbols are used in the present description or claims, each of them, independently of the others, may or may not be replaced by a more specific definition given hereinabove or hereinbelow—in the case of replacement of one or more such more general expressions or symbols, preferred embodiments of the invention are obtained.

Manufacturing Process

Compounds of the formula I and of the formula XXI can be obtained by or in analogy to methods that are in principle known in the art.

For example, compounds of the formula I can inter alia be obtained analogously to the method described in W. Ried et al., *Chem. Ber.* 1961, 94, 1051.

For example, a novel compound of the formula IA can be obtained by reducing a corresponding compound of the formula II,

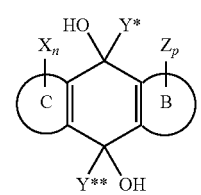

wherein Y* and Y** are ethynyl independently of each other substituted with unsubstituted or substituted hydrocarbyl with up to 40 carbon atoms, unsubstituted or substituted hydrocarbyloxy with up to 40 carbon atoms, hydrocarbylthio with up to 40 carbon atoms, unsubstituted or substituted heteroaryl, unsubstituted or substituted heteroaryloxy, unsubstituted or substituted heteroarylthio, cyano, carbamoyl, wherein Hal represents a halogen atom, substituted amino, halo-$C_1$-$C_8$-alkyl, such as trifluoromethyl, halo, or substituted silyl, while the rings or ring systems labelled A and B and the symbols X, Y, n, m and p have the meanings defined for a compound of the formula IA.

The reduction can, for example, take place in the presence of a metal salt as reductant, such as $SnCl_2$, in an appropriate solvent, e.g. an ether, such as dioxane, or a ketone, such as acetone, in the presence of an acid, e.g. hydrochloric or acetic acid, with or without the presence of water.

A starting material of the formula II can, for example, be prepared from a quinoid compound of the formula III,

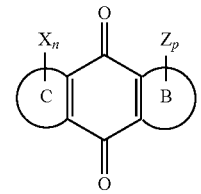

by reacting it with compounds of the formulae IV $$Y^{***}-H \qquad (IV)$$

wherein Y*** is Y* and Y** as defined for a compound of the formula II, in the presence of a strong base sufficient for removal of the acetylenic proton, such as a Grignard reagent, an alkali-metal alcoholate, such as potassium t-butoxide, a lithium amide such as lithium diisopropylamide, or the like in an appropriate solvent, such as tetrahydrofurane, dioxane, diethoxymethane or dimethoxymethane, glyme, diglyme, toluene or anisol or mixtures of two or more thereof, e.g. at temperatures in the range from 0 to 100° C., preferably from 10 to 80° C.

A compound of the formula III wherein ring B and ring C are identical which results in a compound of $C_{2h}$ symmetry can, for example, be obtained by reacting a compound of the formula V,

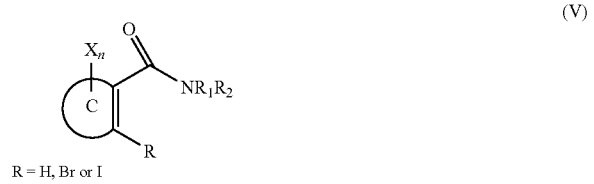

(V)

R = H, Br or I wherein ring C, X and n are as defined for a compound of the formula I and $R_1$ and $R_2$ are independently of the other $C_1$-$C_8$-alkyl or $R_1$ is $C_1$-$C_8$ alkyl and $R_2$ is lower alkoxy such as methoxy or ethoxy (Weinreb amide), in the presence of a lithiating agent such as n-butyllithium or LDA, in an appropriate solvent, e.g. diethyl ether, THF or a hydrocarbon, such as $C_1$-$C_8$-alkanes or also mixtures of two or more of these solvents, preferably at lower temperatures, e.g. in the range from −100 to 50° C., e.g. from −80 to 30° C., which leads under dimerisation to a compound of formula III with $C_{2h}$ symmetry.

Alternatively, (preferably symmetrical) compounds of the formula III can be obtained by reaction of a dialdehyde compound of the formula VIII,

(VII)

wherein ring BC' is a ring completing ring or ring system C and ring or ring system B in a compound of the formula III and X and n are as defined for a compound of the formula I, with a compound of the formula VIII,

(VIII)

under aldol condensation conditions to give a compound or—where it applies—a mixture (which can then be separated according to standard procedures to give the corresponding isomerically pure compound) of compounds of the following formula IIIA which falls under formula III (wherein Z=X and p=n in formula III):

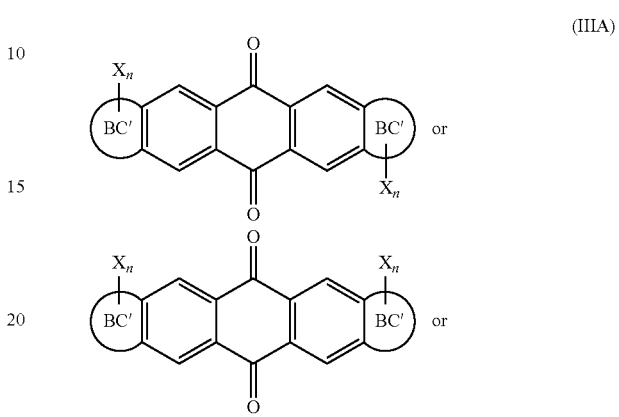

(IIIA)

wherein BC' is a ring or ring system completing ring systems B and C (meaning forming together with the annealed benzo ring a ring system B or C) in a compound of the formula III and X and n are as defined for a compound of the formula I.

For the manufacture of the corresponding ferrocenobenzo compounds of the formula III, as compound of the formula VII a compound of the formula VII*

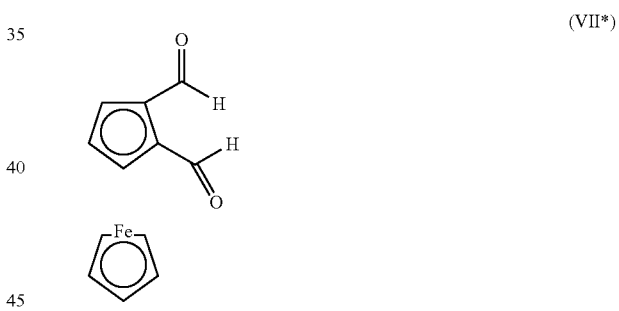

(VII*)

can be used which may be unsubstituted or substituted by X and Z if n and/or p is 1 or more.

Alternatively, (preferably with regard to rings or rings systems B and C un-symmetrical) compounds of the formula III can be obtained by reaction of a dialdehyde compound of the formula VII as given above, wherein ring or ring system BC' is a ring completing ring system C in a compound of the formula III and X and n are as defined for a compound of the formula I, with a compound of the formula VIII*,

(VIII*)

wherein B' is a ring or ring system B as defined under formula I and Z and p are as defined for a compound of the formula I, e.g. under aldol condensation conditions to give a compound or—where it applies—a mixture of compounds (which can then be separated according to standard procedures to give the corresponding isomerically pure compound) of the following formula IIIA which falls under formula III:

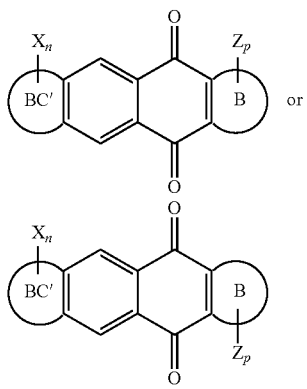

wherein ring or ring system BC' is a ring completing ring or ring system C in a compound of the formula III, ring or ring system B is as defined for a compound of the formula I and X, Z, p and n are as defined for a compound of the formula I.

Still alternatively, compounds of formula (III) may be obtained by Friedel-Crafts acylation following the general scheme below (wherein B, C, X, Y, n and p are as defined for a compound of the formula IA):

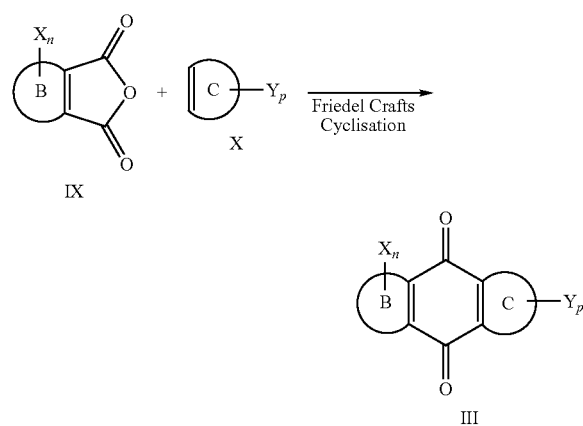

This method allows for the synthesis of both symmetric (ring B=ring C, X=Z, n=p) and asymmetric compounds of the formula III. The reaction (a Friedel-Crafts cyclisation) takes place under customary reaction conditions, e.g. in the presence of a Lewis acids, especially $AlCl_3$, and sulfuric acid or polyphosphoric acid in one or two steps; instead of the anhydride of the formula IX, other active dicarbonic acid derivatives may be used, e.g. mixed anhydrides, carbonic acid halogenides, active esters or the like. As solvents, standard solvents are used. Examples for possible reaction conditions are given e.g. in Zani et al., Bioorg. Med. Chem. 5, 2185 (1997). For example, naphtha[2,3-b]thiophene-4,9-dione can be prepared like this which is a compound of the formula III.

Certain compounds of the formula I, namely those of the formula I*** given in the following reaction scheme, may alternatively be manufactured by Sonogashira coupling starting from a compound of the formula XI,

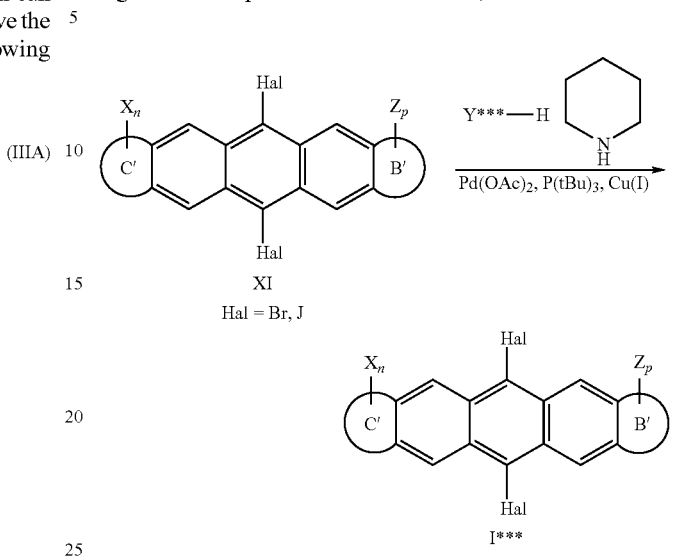

where Y***—H is a compound of the formula IV as defined above, B' and C' are rings complementing a di- or polycyclic ring B and C in a corresponding compound of the formula I, respectively, and X, Z, n and p are as defined for a compound of the formula I, respectively.

Compounds of the formula XI are prepared according to methods that are known in the art, e.g. bromination of precursors not carrying the bromo group, from the corresponding aromatic nitro compounds via reduction, by Sandmeier reaction of the corresponding educts, from the corresponding aromatic carbonic acid amides by Hofmann rearrangement or the like.

A compound of the formula I* can be prepared from a compound of the formula XII, a compound of the formula I** from a compound of the formula XIII according to the following reaction scheme

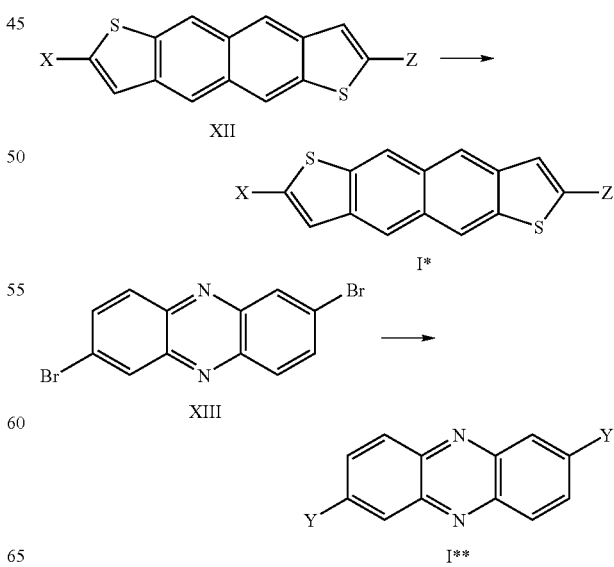

by reaction with a compound of the formula XIV,

X/Z—C≡C—H (XIV)

wherein X/Z—C≡C corresponds to X and Z in a compound of the formula I* or I**, e.g. in the presence of a strong base sufficient for removal of the acetylenic proton, such as a Grignard reagent, an alkali-metal alcoholate, such as potassium tert-butoxide, a lithium amide such as lithium isopropylamide, or the like, e.g. in an appropriate solvent, such as tetrahydrofurane, dioxane, diethoxymethane or dimethoxymethane, glyme, diglyme, toluene or anisol or mixtures of two or more thereof, e.g. at temperatures in the range from 0 to 100° C., preferably from 10 to 80° C.

Other compounds of the formula I, starting materials of the formula IV (which may also be prepared in analogy to the methods described in DE-OS 2 320 528 which is incorporated herein by reference especially concerning the ethynyl compounds and their preparation mentioned therein), of the formula V and VI and of the formula VII and VII, of the formula IX and X, of the formula XII, XIII and XIV, as well as other starting materials, are known in the art, they can be obtained according to methods that are known in the art or they are available commercially.

A compound of the formula XXI can, for example, be prepared
a) by reacting a 9,10-dibromoanthracene compound of the formula XXII,

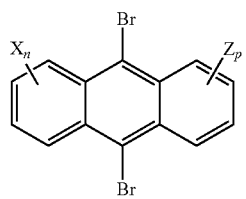

(XXII)

wherein X, Z, n and p are as defined for a compound of the formula XXI, or a substituted derivative thereof carrying, preferably in the presence of an appropriate solvent, e.g. a hydrocarbon, such as toluene, and a tertiary nitrogen base, e.g. triethyl-amine, at preferred temperatures in the range from 0° C. to the reflux temperature of the reaction mixture, with an ethynyl compound of the formula XXIII

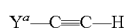

Y$^a$—C≡C—H (XXIII)

wherein Y$^a$ is fluoro- or chloro-substituted hydrocarbyl, under Sonogashira coupling conditions or the like, e.g. in the presence of palladium(II)acetate, triphenylphosphine and copper iodide; or
b) by reacting a compound of the formula XXIV,

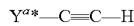

Y$^{a*}$—C≡C—H (XXIV)

wherein Y$^{a*}$ is halo(especially bromo or iodo)-substituted hydrocarbyl, preferably in the presence of an appropriate solvent, such as an ether, e.g. tetrahydrofurane, and/or hydrocarbons, such as hexanes, with a strong base sufficient for removal of the acetylenic proton, such as a Grignard reagent, an alkali-metal alcoholate, such as potassium t-butoxide, a lithium amide, such as lithium diisopropylamide, or the like, to the corresponding deprotonated compound (acetylide), e.g. at temperatures from −90 to 25° C., then reacting the resulting mixture comprising the acetylide with an anthraquinone of the formula XXV,

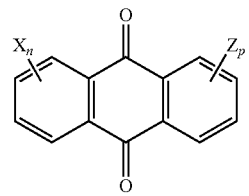

(XXV)

e.g. at temperatures in the range from 0 to 50° C., and reducing resulting diol compound, e.g. with tin(II)-chloride in a mixture of a ketone, e.g. acetone, water and an acid, such as hydrochloric or acetic acid, e.g. at temperatures in the range from 0 to 50° C., to give a compound of the formula XXI.

The starting materials of the formulae XXIII and XXIV are known, can be prepared according to methods that are known in the art and/or are commercially obtainable, as are 9,10-dibromoanthracene and anthraquinone. The anthraquinones of the formula XXV, for example, can be prepared according to the method described above for the manufacture of a compound of the formula III from a compound of the formula V and a compound of the formula VI, using amides with the appropriate structures instead of the compounds of the formulae V and VI.

For all compounds of the formula I, IA, IB, IC, I*, I** or XXI it is possible to obtain the isomerically pure compounds directly or after separation of the final product or any appropriate precursor according to standard separation procedures, such as chromatography, distribution, crystallisation or the like. For starting materials for the synthesis of compounds of the formula I, where appropriate the same point symmetries can apply as for the final products.

If required, protecting groups can be present in starting materials or intermediates that can be removed after the reaction and allow to avoid that functional groups take part in the reaction that shall not react. Customary reaction groups, their introduction and their removal can be deduced from T. W. Green and G. M. Wuts, Protective Groups in Organic Chemistry, 3$^{rd}$ ed., John Wiley & Sons, Weinheim 1999, and comparable standard textbooks.

It is another object of the present invention to prepare thin films of an organic solvent soluble compound of formula I or of formula XXI by applying a solution of the precursor in an organic solvent onto a substrate and thereafter removing the solvent.

It is yet another object of the present invention to use a thin film of an compound of the formula I or of the formula XXI as defined above or below in a thin film transistor in which said compound film acts as a p-type or n-type semiconductor channel.

Semiconductor Devices

The compounds of the formula I or their preferred versions (compounds of the formula IA, especially of the formula IB or IC) or compounds of the formula XXI can be used as the semiconductor layer in semiconductor devices, especially FETs. There are numerous types of semiconductor devices. Common to all is the presence of one or more semiconductor materials. Semiconductor devices have been described, for example, by S. M. Sze in Physics of Semiconductor Devices, 2.sup.nd edition, John Wiley and Sons, New York (1981). Such devices include rectifiers, transistors (of which there are many types, including p-n-p, n-p-n, and thin-film transistors), light emitting semiconductor devices (for example, organic light emitting diodes), photoconductors, current limiters, thermistors, p-n junctions, field-effect diodes, Schottky diodes, and so forth. In each semiconductor device, the semiconductor material is combined with one or more metals or insulators to form the device. Semiconductor devices can be prepared or manufactured by known methods such as, for example, those described by Peter Van Zant in Microchip Fabrication, Fourth Edition, McGraw-Hill, New York (2000).

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, 2nd.sup. edition, John Wiley and Sons, page 492, New York (1981)). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise inorganic glasses, ceramic foils, polymeric materials (for example, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive polymers also can be used, for example polyaniline or poly(3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material or a polymeric dielectric layer.

Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these materials can be used for the gate dielectric.

Alternatively, the gate dielectric may comprise an organic polymeric dielectric layer. A number of organic polymers have been considered as dielectric materials. These include polyimides, parylene C, crosslinked cyclobutene, and cyanoethylpullulan. See, for example C. D. Sheraw et al. "Spin-on polymer gate dielectric for high performance organic thin film transistors", Materials Research Society Symposium Proceedings v. 558, Materials Research Society, Warrendale, Pa., USA, pages 403-408 (2000), U.S. Pat. No. 6,265,243 (Katz);U.S. Pat. No. 5,347,144 (Garnier) and Janos Veres et al. "Gate Insulators in Organic Field-Effect Transistors" in Chem. Materials 2004.

The source electrode and drain electrode are separated from the gate electrode by the gate dielectric, while the organic semiconductor layer can be over or under the source electrode and drain electrode. The source and drain electrodes can be any useful conductive material. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or printing, e.g. ink jet printing. The patterning of these electrodes can be accomplished by known methods such as shadow masking, additive photolithography, subtractive photolithography, printing, microcontact printing, pattern coating and/or laser induced thermal imaging (LITI).

The present invention further provides a thin film transistor device comprising a plurality of electrically conducting gate electrodes disposed on a substrate; a gate insulator layer disposed on said electrically conducting gate electrodes;
an organic semiconductor layer disposed on said insulator layer substantially overlapping said gate electrodes; and
a plurality of sets of electrically conductive source and drain electrodes disposed on said organic semiconductor layer such that each of said sets is in alignment with each of said gate electrodes;
wherein said organic semiconductor layer is formed from a compound of the formula I or more preferably of the formula IA, especially of the formula IB or IC as defined above or below generally or preferably more specifically, or from a compound of the formula XXI as defined above or below generally or preferably more specifically.

The present invention further provides a process for preparing a thin film transistor device comprising the steps of:
depositing a plurality of electrically conducting gate electrodes on a substrate;
depositing a gate insulator layer on said electrically conducting gate electrodes;
depositing a layer of a compound of the formula I or of the formula XXI on said insulator layer such that said layer of compound of the formula I or the formula XXI substantially overlaps said gate electrodes;
depositing a plurality of sets of electrically conductive source and drain electrodes on said layer such that each of said sets is in alignment with each of said gate electrodes; thereby producing the thin film transistor device.

Any suitable substrate can be used to prepare the thin films of the compounds of the formula I or the formula XXI of the present invention as well as the thin films of the precursor thereof. For example, the substrate used to prepare the above thin films is a metal, silicon, plastic, glass or coated glass.

Alternatively, a TFT is fabricated by, for example, by solution deposition of a compound of the formula I or the formula XXI on a highly doped silicon substrate covered with a thermally grown oxide layer followed by vacuum deposition and patterning of source and drain electrodes.

In yet another approach, a TFT is fabricated by deposition of source and drain electrodes on a highly doped silicon substrate covered with a thermally grown oxide and then solution deposition of a compound of the formula I or the formula XXI to form a thin film.

The gate electrode can also be a patterned metal gate electrode on a substrate or a conducting material such as, a conducting polymer, which is then coated with an insulator applied either by solution coating or by vacuum deposition on the patterned gate electrodes. The insulator can be a material, such as, an oxide, nitride, or it can be a material selected from the family of ferroelectric insulators, including but not limited to $PbZr_xTi_{1-x}O_3$ (PZT), $Bi_4Ti_3O_{12}$, $BaMgF_4$, $Ba(Zr_{1-x}Ti_x)O_3$ (BZT), or it can be an organic polymeric insulator.

Any suitable solvent can be used to dissolve a compound of the formula I or the formula XXI, provided it is inert, can dissolve at least some of material and can be removed from the substrate by conventional drying means (e.g. application of heat, reduced pressure, airflow etc.). Suitable organic solvents for processing the semiconductors of the invention include, but are not limited to, aromatic or aliphatic hydrocarbons, halogenated such as chlorinated hydrocarbons, esters, ethers amides, such as chloroform, tetrachloroethane, tetrahydrofuran, toluene, ethyl acetate, methyl ethyl ketone, dimethyl formamide, dichlorobenzene, propylene glycol monomethyl ether acetate (PGMEA) and mixtures thereof. The solution is then applied by a method, such as, spin-coating, dip-coating, screen printing, microcontact printing, doctor blading or other solution application techniques known in the art on the substrate to obtain thin films of the semiconducting material or its precursor.

Preferably, the thickness of the organic semiconductor layer is in the range of from about 5 to about 200 nm, especially the thickness is in the range of from about 10 to about 30 nm.

The organic semiconductor layer of the semiconductor device according to the invention can be provided by any useful means, such as, for example, vapor deposition and printing techniques. Some of the compounds of the formula I or XXI (for example, those bearing sufficiently large alkyl groups such as two dodecyl, nonyl, or hexyl substituents, especially unbranched ones which are uninterrupted, or branched or unbranched interrupted groups such as alkyls branched in α-position to the heterofunction) are sufficiently soluble in organic solvents and can be solution deposited (for example, by spin coating, dip coating, ink jet printing, casting, or other known techniques).

The compounds of the formula I or the formula XXI can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, and the like.

The invention relates especially to the subject matter in the claims, the dependent claims defining preferred embodiments of the invention. The claims are incorporated into the description by reference. The invention also especially relates to the compounds mentioned in the examples, their use as semiconductors and semiconductor devices comprising these compounds. Preferred are those embodiments of the invention in which, where a compound of the formula I is mentioned (be it as such, for use or as component of a semiconductor device), an (essentially) isomerically pure compound of the formula I is meant.

The following examples are for illustrative purposes only and are not to be construed to limit the instant invention in any manner whatsoever. Room temperature depicts a temperature in the range 20-25° C. Percentages are by weight unless otherwise indicated.

Abbreviations used in the examples or elsewhere:
Calc. Calculated (theoretical)
DMSO dimethylsulfoxide
DSC Differential Scanning Calorimetrie
h hour(s)
LDA lithium diisopropylamide
min minute(s)
m.p. melting point
MS mass spectroscopy
NMR Nuclear Magnetic Resonance
THF tetrahydrofurane

PREPARATION EXAMPLES

Educt 1: Dibenzo[d,d']benzo[1,2-b;4,5-b']dithiophene-6,12-dione

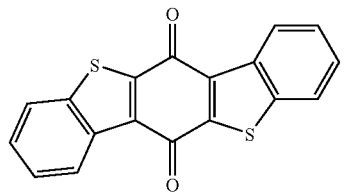

To a solution of benzo[b]thiophene-3-carboxylic acid diethylamide (14.0 g, 60 mmol) in diethyl ether (120 ml) is cooled to −78° C. Under an inert atmosphere a solution of n-butyllithium in hexanes (41.3 ml 1.6 N solution, 66 mmol) is then added within 15 minutes. There is a slight increase of the temperature by 3° C., and the mixture is allowed to stir for another 10 minutes at −78 . . . −75° C. Then the mixture is allowed to warm to ambient temperature. After ca. 1.5 hours a reddish brown suspension is formed which is stirred for another 17 hours. Then water (150 ml) is carefully added to the mixture and also chloroform (50 ml). The mixture is stirred rapidly for 15 minutes, and the solid is filtered off, washed with water, dried and recrystallized from DMSO (50 ml) to give the product as orange brown needles mp=315° C.

Educt 2: 6,12-Bis-(4-tert-butyl-phenylethynyl)-6,12-dihydrodibenzo[d,d']benzo[1,2-b;4,5-b']dithiophene-6,12-diol

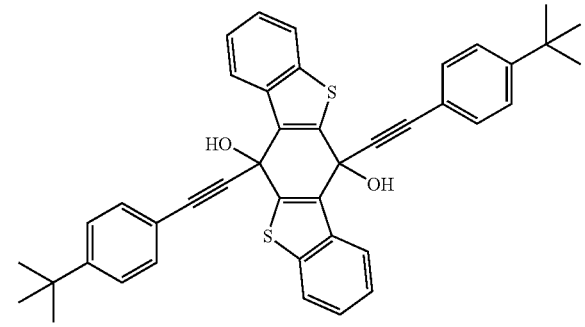

In a flame dried flask, a solution of di-isopropylamine (3.04 g, 30 mmol) in THF (80 ml) is cooled to −78° C., and n-butyllithium (14.1 ml 1.6 N solution, 22.5 mmol) is added within 10 minutes. The pale yellow solution is stirred for another 10 minutes at −78° C. and then allowed to warm to ambient temperature and stirred for another 15 minutes to give a solution of LDA.

In another flame dried flask, a solution of 1-tert-butyl-4-ethynyl-benzene (3.56 g, 22.5 mmol) in THF (20 ml) is prepared, and the freshly prepared LDA is added to this solution within 10 minutes. The temperature is maintained in the range between 23-26° C. by cooling, and the solution is stirred for another 10 minutes at ambient temperature. Then dibenzo[d, d']benzo[1,2-b;4,5-b']dithiophene-6,12-dione (educt 1) (2.40 g, 7.5 mmol) is added as a solid, and the mixture heated to 50° C. and stirred for 52 hours at this temperature. The clear red solution is poured carefully into water (100 ml), and the product extracted with chloroform (80 ml). The aqueous layer is extracted again with chloroform (80 ml), and the combined organic layers are washed with brine and dried (sodium sulphate). Removal of the solvent leaves the crude product as light brown crystals. The crystals are refluxed in methanol (50 ml) (incompletely dissolved) and the mixture allowed to crystallise over night. The solid is then filtered off and washed with methanol thrice (7 ml each time) and dried in vacuo to give the product as beige crystals. $^1$H-NMR (CDCl$_3$, 300 MHz) δ 1.29 (s, 9H, C(CH$_3$)$_3$); 3.09 (s, 1H, OH); 7.27, 7.36 (AA'BB', 4H, Ph H); 7.43, 7.48 (2 "tr", 1H each), 7.89 pp (d, J=6.5 Hz, 1H), 8.54 (d, J=8.2 Hz, 1H) benzothiophene H. $^{13}$C-NMR (CDCl$_3$, 75 MHz) δ 31.47 (C(CH$_3$)$_3$); 35.17 (q, C(CH$_3$)$_3$); 64.79 (q, COH); 87.80, 88.69 (2 q, C≡C); 118.96 (q), 123.03, 124.84, 125.13, 125.77 (benzothiophene CH); 125.46, 131.76 (Ph CH); 130.90 (q), 136.15 (q), 140.37 (q), 144.11 (q), 152.48 (q).

Example 1

6,12-Bis-(4-tert-butyl-phenylethynyl)dibenzo[d,d']benzo[1,2-b;4,5-b']dithiophene

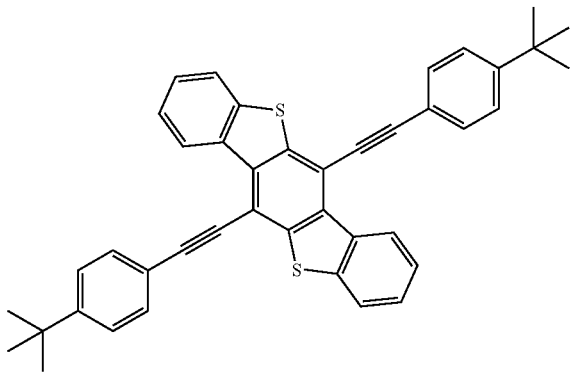

A solution of tin(II)chloride dehydrate (1.82 g, 8.05 mmol) in glacial acetic acid (30 ml) is added within ten minutes to a solution of 6,12-bis-(4-tert-butyl-phenylethynyl)-6,12-dihydro-dibenzo[d,d']benzo[1,2-b;4,5-b']dithiophene-6,12-diol (educt 2) in acetone (30 ml). There is a slight temperature increase (8° C.), and formation of a yellow suspension takes place. This suspension is stirred over night at ambient temperature, and then the solid is filtered off. The solid is then washed with water/glacial acetic acid (twice, 30 ml 1:1 v:v), water (twice with 30 ml), and twice with acetone (30 ml). The residue is then dried to give crude product which is recrystallised from anisol (65 ml). The product is filtered off, washed with anisol (8 ml), toluene (2 times 8 ml) and hexane (twice ca. 10 ml) and dried to give the title product as yellow crystals. Mp. (DSC) 349-350° C., MS (m/z 602 (100%), correct isotopic pattern), elementary analysis: C, 84.61%; (calcd. 83.68%); H, 5.89%; (calcd. 5.68%). $^1$H-NMR (CDCl$_3$, 300 MHz) δ 1.33 (s, 9H, C(CH$_3$)$_3$); 7.41-7.47 (m, 4H, 2 Ph H, 2 benzothiophene H); 7.66 (AA'BB', 2H, 2 Ph H); 7.84 (m, 1H), 9.15 (m, 1H) (2 benzothiophene H).

Educt 3: 6,12-Bis-[(triisopropylsilanyl)-ethynyl]-6,12-dihydro-dibenzo[d,d']benzo[1,2-b;4,5-b']dithiophene-6,12-diol

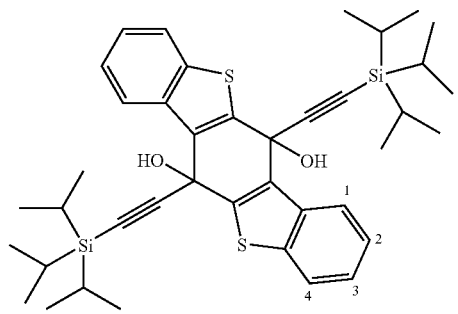

LDA is prepared as described for educt 2 from di-isopropylamine (1.62 g, 16 mmol) and n-butyllithium (7.5 ml 1.6N solution in hexanes, 12.0 mmol) in THF (10 ml).

In another flame dried flask, a solution of tri-isopropylsilane (2.19 g, 12 mmol) in THF (15 ml) is prepared, and the freshly prepared LDA is added to this solution within 10 minutes. The temperature is maintained in the range between 23-26° C. by cooling, and the solution is stirred for another 10 minutes at ambient temperature. Then dibenzo[d,d']benzo[1, 2-b;4,5-b']dithiophene-6,12-dione (educt 1) (1.28 g, 4 mmol) is added as a solid, and the mixture heated to 50° C. and stirred for 52 hours at this temperature. The clear deep yellow solution is poured carefully into water (50 ml), and the product extracted with chloroform (40 ml). The aqueous layer is extracted again with chloroform (40 ml), and the combined organic layers are washed with brine and dried (sodium sulphate). Removal of the solvent leaves the crude product as yellow crystals, which are otherwise pure (2 stereoisomers 1.0:0.95) by NMR. $^1$H-NMR (CDCl$_3$, 300 MHz) δ 1.03-1.10 m (m, 21H, CH(CH$_3$)$_2$); 7.36-7.46 (m, 2H, H-2, H-3); 7.89 (m, 1H, H-4); 8.52 (m, 1H, H-1). $^{13}$C-NMR (CDCl$_3$, 75 MHz) δ 11.56, 11.62 (CHMe$_2$); 18.84, 18.92 (CH(CH$_3$)$_2$); 64.33, 64.38 (C-6); 89.56, 89.65 (alkine-C); 95.01 (alkine-C); 122.83, 122.89 (CH); 124.33, 124.43 (CH); 125.27, 125.43

(CH); 125.441, 125.61 (CH); 130.38, 130.75 (C); 136.03, 136.16 (C); 140.20, 140.28 (C); 144.89, 144.11 (C).

Example 2

6,12-Bis-[(triisopropylsilanyl)-ethynyl]-dibenzo[d,d']benzo[1,2-b;4,5-b']dithiophene

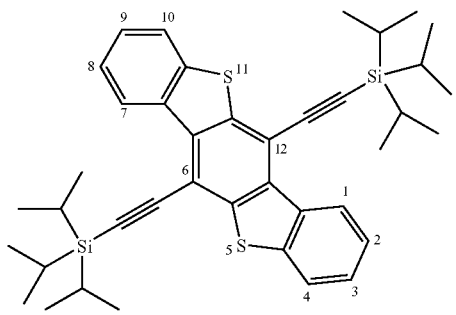

A solution of tin(II)chloride dehydrate (2.59 g, 11.5 mmol) in 50% acetic acid (40 ml) is added within ten minutes to a solution of 6,12-bis-[(triisopropylsilanyl)-ethynyl]-6,12-dihydro-dibenzo[d,d']benzo[1,2-b;4,5-b']dithiophene-6,12-diol (educt 3) in acetone (35 ml). There is a slight temperature increase (2-3° C.), and formation of a yellow suspension takes place. This suspension is stirred over night at ambient temperature, and then the solid is filtered off. The solid is then washed with 50% acetic acid (30 ml), water (twice with 40 ml), and acetone (2*40 ml). The residue is then dried to give crude product which is recrystallised from toluene (15 ml). The product is filtered off, washed with toluene (10 ml), and hexane (10 ml). After drying, the title product is obtained as pale yellow crystals. Mp. (DSC) 155° C. (broad probably phase transition), 208° C. (sharp, probably melting point). $^1$H-NMR (CDCl$_3$, 300 MHz) δ 1.31-1.336 (m (higher order), 21H, CH(CH$_3$)$_2$); 7.48 (m, 1H, H-2), 7.53 (m, 1H, H-3), 7.92 (d, 1H, H-4); 9.37 (d, 1H, H-1). $^{13}$C-NMR (CDCl$_3$, 75 MHz) δ 11.92 (CH); 19.22 (CH$_3$); 103.42, 106.36 (C≡C); 112.56 (C-6); 122.78 (C-4); 124.33 (C-2); 125.16 (C-1); 127.46 (C-3); 132.78 (C-6a); 135.49 (C-6b); 140.47 (C-4-a); 143.30 (C-5a).

Educt 4: 6,12-Bis-triethylsilanylethynyl-6,12-dihydro-dibenzo[d,d']benzo[1,2-b;4,5-b']dithiophene-6,12-diol

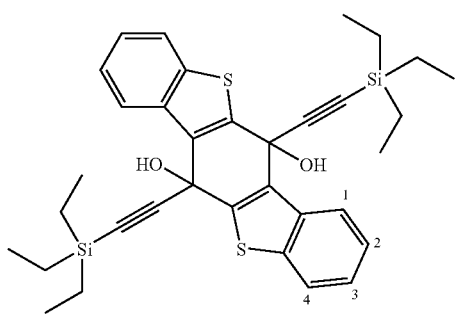

LDA is prepared as described for educt 2 from di-isopropylamine (3.24 g, 32 mmol) and n-butyllithium (15.0 ml 1.6N solution in hexanes, 24 mmol) in THF (20 ml).

In another flame dried flask, a solution of triethylsilane (3.37 g, 24 mmol) in THF (25 ml) is prepared, and the freshly prepared LDA is added to this solution within 15 minutes. The temperature is maintained in the range between 23-30° C. by cooling, and the solution is stirred for another 10 minutes at ambient temperature. Then dibenzo[d,d']benzo[1,2-b;4,5-b']dithiophene-6,12-dione (educt 1) (2.56 g, 8 mmol) is added as a solid, and the mixture heated to 50° C. and stirred for 20 hours at this temperature. The slightly turbid orange solution is poured carefully into water (100 ml), and the product is extracted with chloroform (100 ml). The aqueous layer is extracted again with chloroform (40 ml), and the combined organic layers are washed with brine and dried (sodium sulphate). Removal of the solvent leaves the crude product as brown-yellow crystals. $^1$H-NMR (CDCl$_3$, 300 MHz) δ 0.61 (q, 6H, SiCH$_2$); 0.96 (tr, 9H, CH$_3$); 7.36-7.46 (m, 2H, H-2, H-3); 7.88 (m, 1H, H-4); 8.48 (m, 1H, H-1). $^{13}$C-NMR (CDCl$_3$, 75 MHz) δ 4.53 (SiCH$_2$); 7.81 (CH$_3$); 64.41 (COH); 90.85 (alkine-C); 105.82 (alkine-C); 122.93 (CH); 124.51 (CH); 125.29 (CH) 125.71 (CH); 130.69 (C); 135.97 (C); 140.32 (C); 143.93 (C).

Example 3

6,12-Bis-triethylsilanylethynyl-dibenzo[d,d']benzo[1,2-b;4,5-b']dithiophene

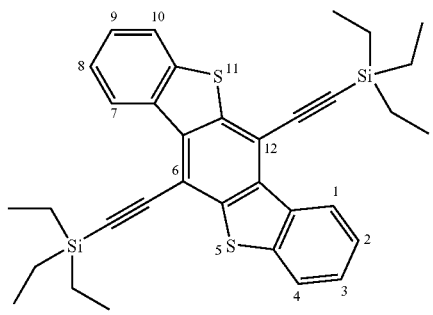

A solution of tin(II)chloride dehydrate (2.08 g, 9.2 mmol) in 50% acetic acid (35 ml) is added within ten minutes to a solution of 6,12-bis-triethylsilanylethynyl-6,12-dihydro-dibenzo[d,d']benzo[1,2-b;4,5-b']dithiophene-6,12-diol (educt 4) (2.40 g, 6 mmol) in acetone (30 ml). There is a slight temperature increase (2-3° C.), and formation of a yellow suspension takes place. This suspension is stirred over night at ambient temperature, and then the solid is filtered off. The solid is then washed with 50% acetic acid (30 ml), water (twice with 40 ml), and acetone (2*40 ml). The residue is then dried to give crude product which is filtered over a pad of silica (60 g) with chloroform to give product which is recrystallised from ethyl acetate (40 ml). The product is filtered off, washed with ethyl acetate (2*10 ml), and hexane (10 ml). After drying, the title product is obtained as yellow crystals. Mp. (DSC) 82° C. and 204° C. $^1$H-NMR (CDCl$_3$, 300 MHz) δ 0.92 (q, 6H, SiCH$_2$); 1.26 (tr, 9H, CH$_3$); 7.48 (m, 1H, H-2), 7.51 (m, 1H, H-3), 7.91 (d, 1H, H-4); 9.29 (d, 1H, H-1). $^{13}$C-NMR (CDCl$_3$, 75 MHz) δ 4.95 (CH$_2$); 8.10 (CH$_3$); 102.69, 107.26 (C≡C); 112.46 (C-6); 122.74 (C-4); 124.39

(C-2); 125.05 (C-1); 127.47 (C-3); 132.72 (C-6a); 135.49 (C-6b); 140.53 (C-4-a); 143.08 (C-5a).

Educt 5: 6,12-Bis-trimethylsilanylethynyl-6,12-dihydro-dibenzo[d,d']benzo[1,2-b;4,5-b']dithiophene-6,12-diol

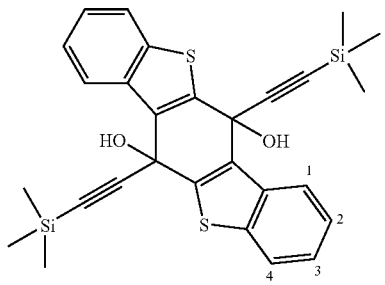

LDA is prepared as described for educt 2 from di-isopropylamine (2.42, 24 mmol) and n-butyllithium (11.25 ml 1.6N solution in hexanes, 18.0 mmol) in THF (15 ml).

In another flame dried flask, a solution of trimethylsilane (1.77 g, 18 mmol) in THF (25 ml) is prepared, and the freshly prepared LDA is added to this solution within 15 minutes. The temperature is maintained in the range between 23-30° C. by cooling, and the solution is stirred for another 10 minutes at ambient temperature. Then dibenzo[d,d']benzo[1,2-b;4,5-b']dithiophene-6,12-dione (educt 1) (1.92 g, 6 mmol) is added as a solid, and the mixture heated to 50° C. and stirred for 52 hours at this temperature. The beige suspension is poured carefully into water (50 ml), and the product is extracted with chloroform (50 ml). The organic layer is washed with water (50 ml) and brine (50 ml) and dried (sodium sulphate). Removal of the solvent leaves the crude product as beige crystals (excess is HN(i-Pr)$_2$). $^1$H-NMR (CDCl$_3$, 300 MHz) δ 0.17 (q, 6H, SiCH$_3$); 7.41-7.50 (m, 2H, H-2, H-3); 7.89 (m, 1H, H-4); 8.47 (m, 1H, H-1). $^{13}$C-NMR (CDCl$_3$, 75 MHz) δ 0.00 (SiCH$_3$); 64.34 (COH); 92.80 (alkine-C); 104.79 (alkine-C); 122.89 (CH); 124.53 (CH); 125.28 (CH) 125.68 (CH); 130.79 (C); 136.05 (C); 140.32 (C); 143.87 (C).

Example 4

6,12-Bis-trimethylsilanylethynyl-dibenzo[d,d']benzo[1,2-b;4,5-b']dithiophene

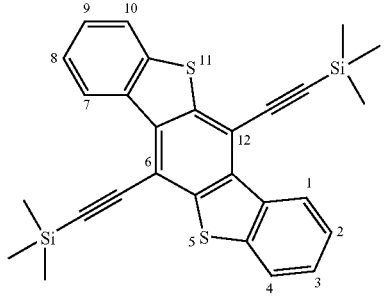

A solution of tin(II)chloride dehydrate (3.11 g, 9.2 mmol) in 50% acetic acid (50 ml) is added within ten minutes to a solution of 6,12-bis-trimethylsilanylethynyl-6,12-dihydro-dibenzo[d,d']benzo[1,2-b;4,5-b']dithiophene-6,12-diol (educt 5) (3.1 g, 6 mmol) in acetone (45 ml). There is a slight temperature increase (2-3° C.), and formation of a yellow suspension. This suspension is stirred over night at ambient temperature, and then the solid is filtered off. The solid is then washed with 50% acetic acid (twice with 30 ml), water (twice with 40 ml), and acetone (2*50 ml). The residue is then dried to give crude product which is filtered over a pad of silica (60 g) with chloroform to give product which is recrystallised from chloroform (35 ml). The product is filtered off, washed with chloroform (10 ml), and hexane (20 ml). After drying, the title product is obtained as yellow crystals. Mp. (DSC) 278° C. and 285° C. $^1$H-NMR (CDCl$_3$, 300 MHz) δ 0.49 (s, 9H, SiCH$_3$); 7.48-7.56 (m, 2H, H-2, H-3), 7.91 (d, 1H, H-4); 9.20 (d, 1H, H-1). $^{13}$C-NMR (CDCl$_3$, 75 MHz) δ 0.28 (CH$_3$); 101.79, 109.51 (C≡C); 112.56 (C-6); 122.93 (C-4); 124.66 (C-2); 125.14 (C-1); 127.72 (C-3); 132.91 (C-6a); 136.63 (C-6b); 140.73 (C-4-a); 143.11 (C-5a).

Educt 6: Anthra[2,3-b]benzo[6,7-b']thiophene-5,11-dione

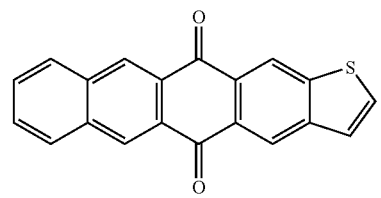

To a solution of 1,4-dihydroxyanthracene (4.2 g, 20 mmol) and thiophene-2,3-dicarboxaldehyde in ethanol (50 ml) at ambient temperature, a 4 M aqueous NaOH solution (1 ml) is added. The reaction mixture is stirred for 16 hours at ambient temperature. The brown precipitate is collected by filtration and washed sequentially with water, ethanol and acetone (each 50 ml), dried and recrystallized from DMF (70 ml) to give the product as fluffy orange needles.

Example 5

5,11-bis(triethylsilylethinyl)anthra[2,3-b]-benzo[6,7-b']thiophene

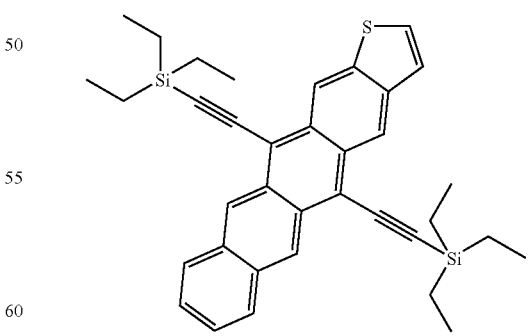

A flame dried flask is charged with triethylsilylacetylene (2.69 g, 19.2 mmol) and 100 ml dry THF and cooled to −78° C. Butyllithium (2.7 M in Heptane; 6.3 ml, 17 mmol) is added, and the mixture is stirred for 45 minutes at −78° C. Then anthra[2,3-b]benzo[6,7-b']thiophene-5,11-dione (educt 6) (1.00 g, 3.2 mmol) is added at once as solid. The reaction mixture is slowly allowed to warm-up to ambient temperature and stirred for 16 h at this temperature. Then a solution of tin(II)chloride (5 g) in 4M HCl (12 ml) is added and the mixture is stirred for 1 hour at 50° C. Then saturated sodium carbonate solution (10 ml) is added and the reaction mixture is filtered over a short pad of hyflo. The filtrate is evaporated to dryness and the resulting dark purple solid is purified by column chromatography (silica gel, eluent:hexane-DCM 4:1). The resulting crystals are twice recrystallized from acetone and dried to give the title product as dark purple plates.

$^1$H-NMR (CDCl$_3$, 300 MHz) δ 0.95 (q, 12H, CH$_2$); 1.30 (tr, 18H, CH$_3$); 7.43 (m, 2H); 7.45 (d, J=5.5 Hz, 1H (thiophene)), 7.53 (d, J=5.5 Hz, 1H (thiophene); 8.00 (m, 2H), 9.09 (s, 1H ("benzothiophene")); 9.14 (s, 1H, ("benzothiophene")); 9.27 (s, 2H ("naphtene")).

Example 6

Further Compounds of the Formula I

Further compounds of the formula I useful e.g. in semiconductor devices:

The following compounds are prepared in analogy to the methods hereinbefore described and independently of each other used as semiconductors in a semiconductor device:

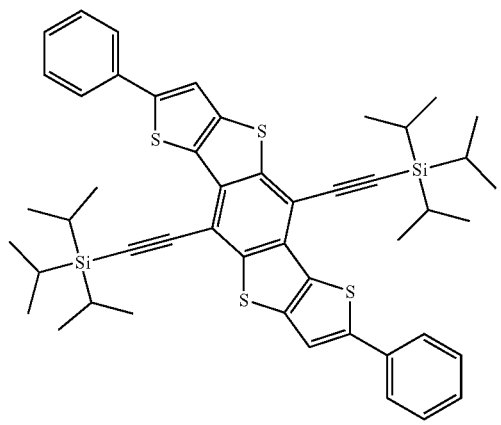

-continued

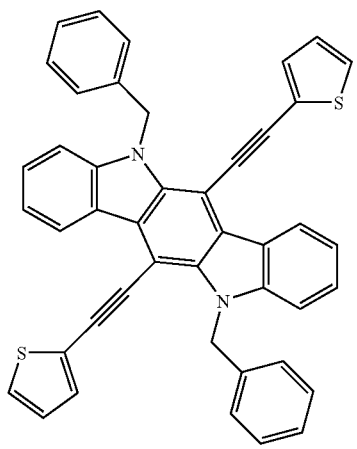

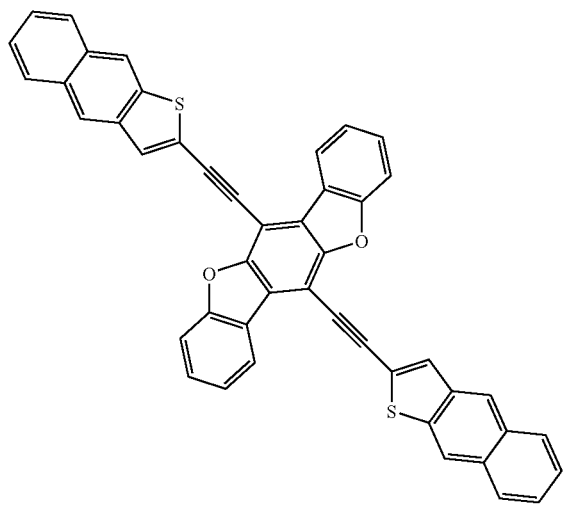

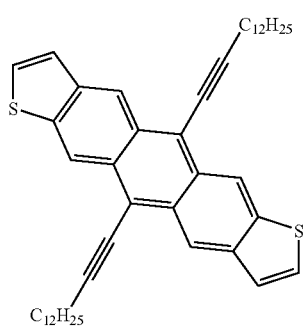

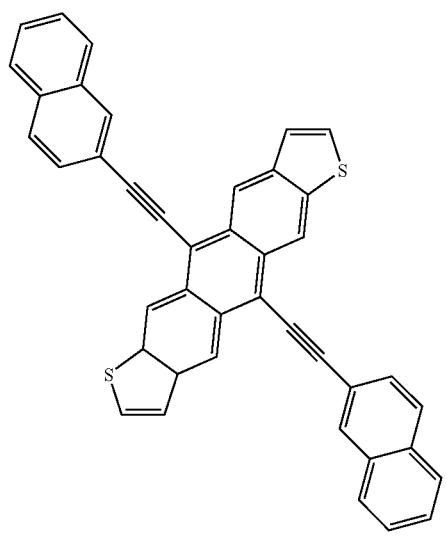

39
-continued
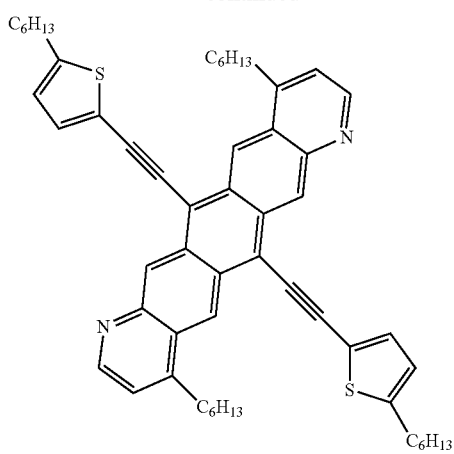
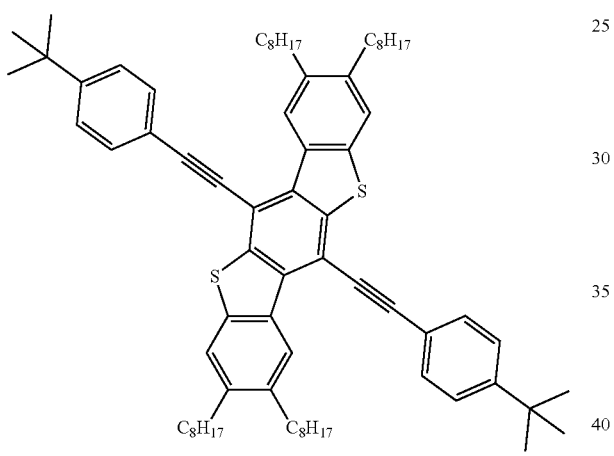
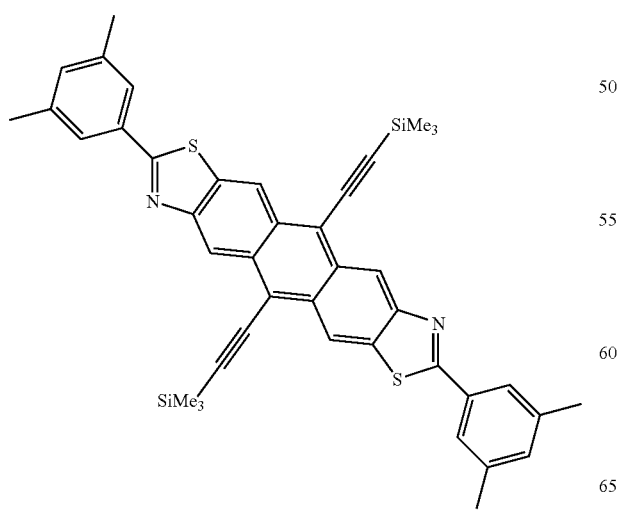
40
-continued
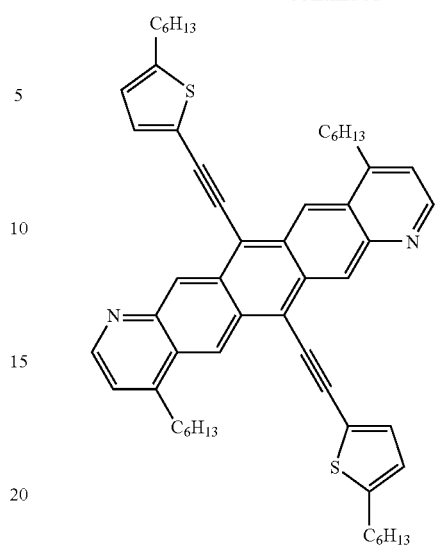
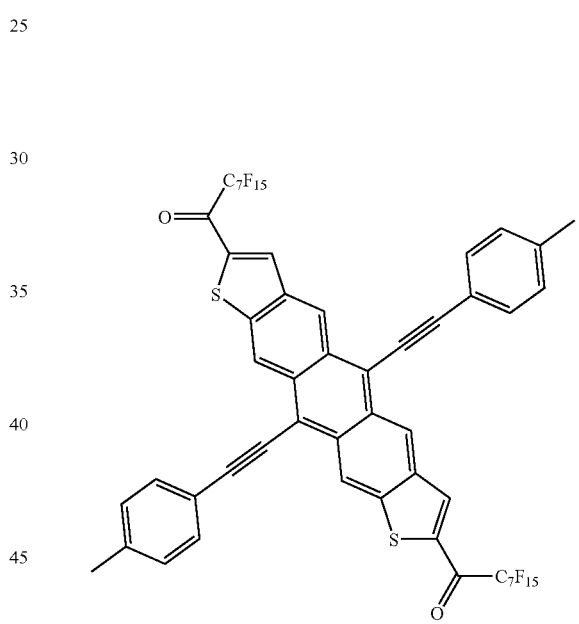
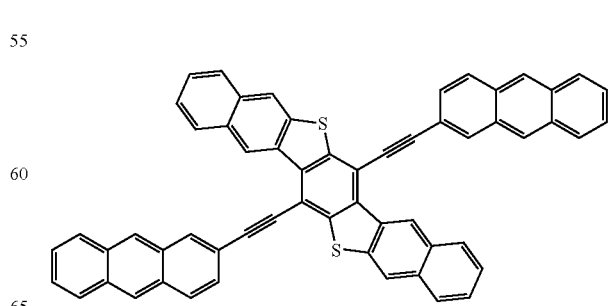

-continued

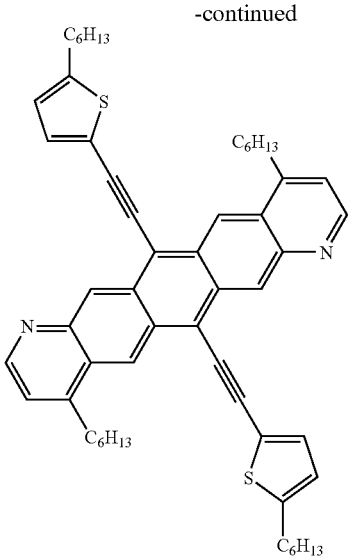

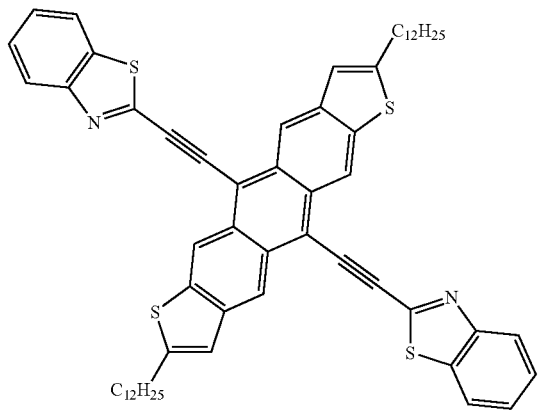

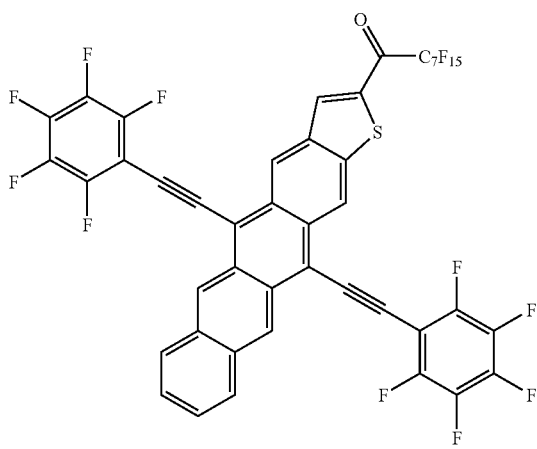

Example 7

9,10-Bis-(4-chloro-phenylethynyl)anthracene

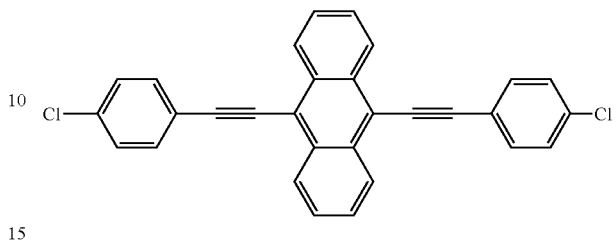

A flask is charged with 9,10-dibromoanthracene (3.36 g, 10 mmol) and a mixture of toluene/triethyl amine (1:2 v:v, 25 ml). The flask is purged with argon for 15 minutes, and the mixture is then heated at reflux. Then p-chlorophenylacetylene (3.42 g, 25 mmol) is added, and the mixture is kept at reflux for five minutes. The obtained yellow suspension is allowed to cool to ambient temperature, and under an atmosphere of argon a mixture of palladium(II)acetate (33.7 mg, 0.15 mmol), triphenyl phosphine (98.4 mg, 0.375 mmol), and copper iodide (34.3 mg, 0.18 mmol) is added. The mixture (brown suspension) is then again heated at reflux for one hour. During this time, the mixture becomes very viscous. Another 15 ml of the toluene/triethylamine mixture is added, and the mixture is stirred for another three hours at ambient temperature, filtered, and the filter cake washed with ether (100 ml). The filter cake is triturated with refluxing methanol (50 ml), and the solid is filtered, washed thrice with methanol (10 ml each) and recrystallised from toluene (180 ml) to give orange crystals. $^1$H-NMR (300 MHz, DMSO-D$_6$) δ 7.62, 7.93 (p-chlorophenyl group); 7.81 (m), 8.66 (m) (anthracene group). DSC: mp=268° C., decomposition at 281° C. MS: m=446 with correct isotope pattern, 410, 374, 348, 322, 300, 274, 248 (vw), 223, 205 (vw), 187.

Transistor data: mobility $4·10^{-4}$ Vs/cm$^2$, threshold voltage −12.3 V, on/off ratio $9.9×10^6$.

Educt 7: 9,10-Bis-(4-bromo-phenylethynyl)-9,10-dihydro-anthracene-9,10-diol

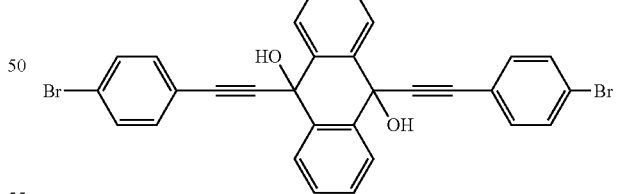

A solution of di-isopropylamine (6.07 g, 60 mmol) in dry THF (30 ml) is cooled to −78° C., and then a solution of n-butyl lithium (28.2 ml 1.6 N solution in hexanes, 45 mmol) is added within 12 minutes. The mixture is stirred for 10 minutes at −78° C. and then allowed to warm to ambient temperature and stirred for another 15 minutes. This solution is added at room temperature to a solution of 4-bromophenylacetylene (8.14 g, 45 mmol) in dry THF (30 ml) within 10 minutes, and after re-cooling to 25° C., anthraquinone (3.12 g, 15 mmol) is added as solid within 5 minutes. The mixture is stirred at ambient temperature for two days. As the reaction is still incomplete (ca. 25% mono-ol, 75% diol by TLC), the mixture is heated at 50° C. for another six hours. Then the solvent is removed at the rotavapor, and to the residue chloroform (ca. 150 ml) and water (ca. 150 ml) are added, and the mixture is stirred for one hour. The chloroform is then removed on the rotavapor, and the solid is filtered off, washed with chloroform (3 times ca. 15 ml) and dried in vacuo to give the title compound in the form of yellow crystals. $^{13}$C-NMR (75 MHz, aceton-D$_6$) δ 67.31, 84.22, 93.14, 121.96, 122.36, 126.33, 128.53, 131.62, 133.35, 139.00.

Example 8

9,10-Bis-(4-bromo-phenylethynyl)anthracene

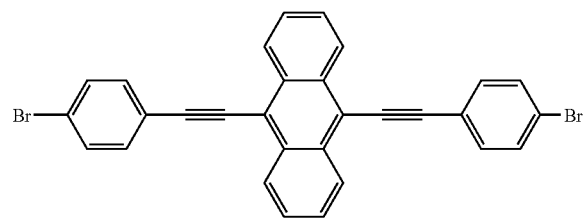

To a suspension of 9,10-bis-(4-bromo-phenylethynyl)-9,10-dihydro-anthracene-9,10-diol (2.0 g, 3.5 mmol) in aceton (25 ml), a solution of tin(II)chloride dihydrate (1.82 g, 8.05 mmol) in a mixture of water (15 ml) and acetic acid (15 ml) is added within 15 minutes. The obtained suspension is stirred for another 2.5 hours at ambient temperature, and then the solid is filtered off to give a first crop the title compound. Over night another crop of product crystallizes from the mother liquors, and the combined crops are recrystallized from anisol (30 ml) to give the title compound as orange needles. DSC: mp=305° C. MS: 534 (correct isotope pattern). Elementary analysis: C, 67.45; (calcd. 67.19); H, 3.23; (calcd. 3.01).

Application Examples

Preparation of Semiconductor Devices and Testing

Bottom-gate thin-film transistor (TFT) structures with p-Si gate (10 Ωcm) are used for all experiments. A high-quality thermal SiO$_2$ layer of 300 nm thickness serves as gate-insulator of $C_i$=11 nF/cm$^2$ capacitance per unit area. Source and drain electrodes are patterned by photolithography directly on the gate-oxide (bottom-contact configuration). Au source/drain electrodes defining channels of width W=2 mm and length L=50 μm are used. Prior to the deposition of the organic semiconductor, the SiO$_2$ surface is derivatized with hexamethyldisilazane (HMDS) by exposing it to saturated silane vapour at 160° C. for 2 hours A compound of the formula I, especially from any one of Examples 1 to 6, or of the formula XXI, especially from Example 7 or 8, is purified in a 3 zone-furnace by train-sublimation at reduced pressure under a constant flow (1×10$^{-3}$ Torr) of argon as a carrier gas. The purified sample is charged in a vacuum vapour deposition apparatus (Balzers) and evaporated from a resistant-heated crucible at a growth rate of 0.1 nm/s on a silicon oxide wafer substrate described above. Chamber pressure typically is 6×10$^{-6}$ Torr at the start and end of the deposition. The film thickness is measured by a quartz crystal monitor to give a total thickness of 50 nm. A Semiconductor Parameter Analyzer (model 4155C from Hewlett Packard, San Jose, Calif.) is used to obtain the results set forth below.

Example 9

Transistor Performance

The thin-film transistors with the compounds of the formula I, I*, I**, V or VI, especially from any one of Examples 1 to 6, or of the formula XXI, especially from Example 7 or 8, can show clear p-type transistor character. From a linear fit to the square root of the saturated transfer characteristics, the field-effect mobility of cm$^2$/Vs is determined (IEEE Standard 1620). With a 300 nm gate-oxide of 11 nF/cm$^2$ capacitance per unit area the transistors show a threshold voltage of about −12.5 to 1.5 V.

The transistors show good on/off current ratios of 10$^4$ to 10$^6$.

A Semiconductor Parameter Analyzer (model 4155C from Hewlett Packard, San Jose, Calif.) is used to obtain the results set forth below.

TABLE 1

Performance of OFET from Example 7 material

| Gate dielectric | Charge Carrier Mobility (cm$^2$/Vs) | Threshold Voltage (V) | Sub-Threshold Slope (V/decade) | On/Off Ratio |
| --- | --- | --- | --- | --- |
| SiO$_2$ | 4*10$^{-4}$ | −12.3 | 0.9 | 9.9*10$^6$ |

Example 10

Transistor from Material from Example 1

A highly doped Si-wafer with 300 nm thermally grown SiO$_2$ is cut and cleaned with hot acetone and hot isopropanol. The sample is immersed in piranha-solution (30% hydrogen peroxide in 70% sulfuric acid) for 10 minutes and thoroughly washed with ultra pure water (18.2 MΩcm). Subsequently, the SiO$_2$ surface is treated with octadecyltrichlorosilane (OTS) by a vapour prime process. For this process, the sample and ~0.3 ml of OTS are heated to 125° C. in a vacuum for three hours. The compound of example 1 is evaporated on the sample through a shadow mask in a high vacuum (base pressure 3×10$^{-6}$ mbar). The substrate is kept at a temperature of 50° C. during the deposition. The deposition rate and the film thickness are measured with a water-cooled quartz crystal in the chamber. 50 nm of the sample compound is deposited at a rate of 0.1-0.3 Å/s. Gold contacts are vacuum-evaporated onto the sample thin-film in a separate chamber resulting in a transistor test structure on the sample with a channel length of 50 μm and a channel width of 14 mm.

The device transfer characteristic and the gate leakage current I$_g$ are measured in a dry He atmosphere using a HP 4155A semiconductor parameter analyzer. For the transfer characteristic, the gate voltage V$_g$ is swept from +100 V to −100 V and back in steps of 0.5 V, while keeping the drain voltage at V$_d$=−50 V. The transfer characteristic is analyzed in terms of non-contact corrected saturation field-effect mobility, onset voltage, threshold voltage, off-current and on-off ratio.

FIG. 1 shows the transfer characteristics of the thin-film device (V$_g$=gate voltage; I$_d$=full line) and, additionally, the gate leakage current (I$_g$=dotted line). The mobility is μ=8×

$10^{-6}$ cm$^2$/Vs. The onset voltage of the device is $V_{on}=-15.4$ V and the threshold voltage is $V_t=-10.3$ V. The off-current $I_{off}$ is $\sim 5\times 10^{-11}$ A and the on-off current ratio $I_{on}/I_{off}$ is 1600.

Example 11

Transistor from Material from Example 2

A bottom contact device with configuration as described before is used. The solution used in fabricating the semiconductor layer comprises 0.5 wt % solution of the sample compound in toluene. Before use, the solution is filtered through 0.45 μm filter. The spin coating is accomplished at a spinning speed of 200 rpm for about 5 seconds in a first step and then 3000 rpm for 30 seconds at ambient conditions. The devices are dried at 80° C. for 5 minutes before evaluation. The following summarizes the average properties from at least 16 transistors for each device: mobility: $3.4\times 10^{-7}$ cm$^2$/Vs; current on-off ratio: $2.2\times 10^4$; threshold voltage: −20.1 V; sub-threshold slope (V/decade): 2.2.

Example 12

Transistor from Material from Example 3

A bottom contact device with configuration as described before is used. The solution used in fabricating the semiconductor layer is comprised of a 1 wt % solution of the compound in chloroform. Before use, the solution is filtered through a 0.2 μm filter. The spin coating is accomplished at a spinning speed of 500 rpm for about 20 seconds in ambient conditions.

The devices are dried at 80° C. for 1 hour before evaluation. The following summarizes the average properties from at least 16 transistors for each device: mobility: $1\times 10^{-7}$ cm$^2$/Vs current on-off ratio: $0.8\times 10^2$ threshold voltage: −14.5 V.

The invention claimed is:

1. A semiconductor device comprising a bis(substituted ethynyl) compound with a tri- or polycyclic aromatic hydrocarbon backbone with heteroatoms wherein the rings that constitute the backbone are annealed to each other via not more than two commonly shared ring atoms, respectively, and the number of the common atoms of the vicinal rings is twice the number of the common side areas, with the proviso that the backbone together with the ethynyl groups have a point symmetry selected from the group consisting of the $C_{2h}$, the $D_{2h}$ and the $C_s$ point symmetry group, which have the formula I

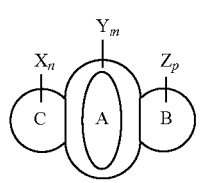

(I)

wherein the ring labelled with A is an aromatic ring with 6 atoms, the ring marked B is a mono- or polycyclic unsaturated ring or ring system or annealed ferrocenobenzo of the subformula I(i)

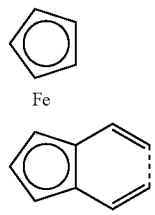

(I(i))

wherein the dotted bond marks the side of the benzo ring annealed to the central ring A in formula I, each annealed to ring A and the ring marked C is a mono- or polycyclic unsaturated ring or ring system or ferrocenobenzo of the subformula I(i) shown above, each annealed to ring A, each of rings or ring systems B and C may also carry a group =S, =O or =C(NQ$_2$)$_2$, where "unsaturated" means having the maximum possible number of conjugated double bonds, and wherein in at least one of the rings or ring systems B and C at least one ring atom is a heteroatom selected from N, NQ, O and S, if the first ring forming or forming part of ring or ring system B and C directly annealed to ring A has six ring atoms in both rings or ring systems B and C;

where the rings or ring systems marked B and C in the compound of the formula I each contain at least one heteroatom, where the heteroatom or heteroatoms are selected from N, NQ, S and O; and each of the rings B and C is selected from the group consisting of the following moieties where the dotted bond marks the side of the ring or ring system annealed to the rest of the molecule:

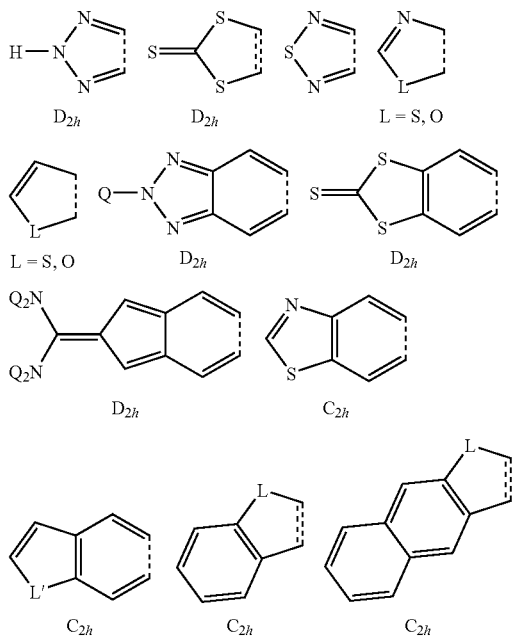

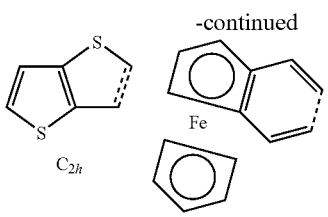

or ring C is selected from the preceding moieties, while ring B is of the formula

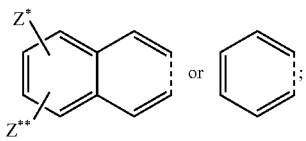

Q is, for each occurrence of Q and each ring independently of the other, hydrogen or an unsubstituted or substituted hydrocarbyl, unsubstituted or substituted hydrocarbylcarbonyl or heteroaryl as defined below for X or Z; or Q is selected from hydrogen, $C_6$-$C_{14}$-aryl, $C_6$-$C_{14}$-aryl-$C_1$-$C_{20}$alkyl, $C_1$-$C_{20}$-alkyl, and $C_1$-$C_{20}$-alkyl;

$Z^*$ and $Z^{**}$ are independently of each other selected from the group consisting of H, unsubstituted or substituted $C_1$-$C_{20}$-alkyl, halogen substituted-$C_1$-$C_{20}$-alkyl, unsubstituted or substituted $C_2$-$C_{20}$-alkenyl, unsubstituted or substituted $C_2$-$C_{20}$-alkynyl, unsubstituted or substituted $C_6$-$C_{14}$-aryl, unsubstituted or substituted heteroaryl with 5 to 14 ring atoms, unsubstituted or substituted $C_6$-$C_{14}$-aryl-$C_1$-$C_{20}$-alkyl, unsubstituted or substituted heteroaryl-$C_1$-$C_{20}$-alkyl, wherein the heteroaryl has 5 to 14 ring atoms, unsubstituted or substituted ferrocenyl, unsubstituted or substituted $C_1$-$C_{20}$-alkanoyl, perfluorinated $C_2$-$C_{10}$-alkanoyl, halo, unsubstituted or substituted $C_1$-$C_{20}$-alkoxy, $C_3$-$C_{20}$-alkenyloxy, $C_3$-$C_{20}$-alkynyloxy, unsubstituted or substituted $C_1$-$C_{20}$-alkylthio, $C_3$-$C_{20}$-alkenylthio, $C_3$-$C_{20}$-alkynylthio, carboxy, unsubstituted or substituted $C_1$-$C_{20}$-alkoxy-carbonyl, unsubstituted or substituted phenyl-$C_1$-$C_{20}$-alkoxy-carbonyl, amino, N-mono- or N,N-di-($C_1$-$C_{20}$-alkyl, $C_1$-$C_{20}$-alkanoyl and/or phenyl-$C_1$-$C_{20}$-alkyl)-amino, cyano, carbamoyl, N-mono- or N,N-di-($C_1$-$C_{20}$-alkyl, $C_1$-$C_{20}$-alkanoyl and/or phenyl-$C_1$-$C_{20}$-alkyl)-carbamoyl and sulfamoyl;

two of the substituents X, Y and Z present in formula I are substituted ethynyl wherein the substitutents are selected from the group consisting of unsubstituted or substituted hydrocarbyl with up to 40 carbon atoms, unsubstituted or substituted hydrocarbyloxy with up to 40 carbon atoms, hydrocarbylthio with up to 40 carbon atoms, unsubstituted or substituted heteroaryl, unsubstituted or substituted heteroaryloxy, unsubstituted or substituted heteroarylthio, cyano, carbamoyl, substituted amino, halo-$C_1$-$C_8$-alkyl, trifluoromethyl, and substituted silyl; or two Y substituents, where each Y, independently of the other, or identically substituted, is selected from substituted ethynyl wherein the substituents are selected from unsubstituted or substituted $C_1$-$C_{20}$-alkyl, unsubstituted or substituted phenyl, unsubstituted or substituted naphthyl, unsubstituted or substituted anthracenyl, substituted silyl which is silyl substituted by two or three moieties selected from $C_1$-$C_{20}$-alkyl, $C_1$-$C_{20}$alkoxy, and phenyl- or naphthyl-$C_1$-$C_{20}$-alkyl;

while the remaining substituents X, Y and/or Z, as far as present, are substitutents selected from the group consisting of unsubstituted or substituted $C_1$-$C_{20}$-alkyl, halogen substituted-$C_1$-$C_{20}$-alkyl, unsubstituted or substituted $C_2$-$C_{20}$-alkenyl, unsubstituted or substituted $C_2$-$C_{20}$-alkynyl other than substituted ethynyl mentioned above, unsubstituted or substituted $C_6$-$C_{14}$-aryl, unsubstituted or substituted heteroaryl with 5 to 14 ring atoms, unsubstituted or substituted $C_6$-$C_{14}$-aryl-$C_1$-$C_{20}$-alkyl, unsubstituted or substituted heteroaryl-$C_1$-$C_{20}$-alkyl, wherein the heteroaryl has 5 to 14 ring atoms, unsubstituted or substituted ferrocenyl, unsubstituted or substituted $C_1$-$C_{20}$-alkanoyl, halo, unsubstituted or substituted $C_1$-$C_{20}$-alkoxy, $C_3$-$C_{20}$-alkenyloxy, $C_3$-$C_{20}$-alkynyloxy, unsubstituted or substituted $C_1$-$C_{20}$-alkylthio, $C_3$-$C_{20}$-alkenylthio, $C_3$-$C_{20}$-alkynylthio, carboxy, unsubstituted or substituted $C_1$-$C_{20}$-alkoxy-carbonyl, unsubstituted or substituted phenyl-$C_1$-$C_{20}$-alkoxy-carbonyl, amino, N-mono-($C_1$-$C_{20}$-alkyl)amino, N,N-di-($C_1$-$C_{20}$-alkyl)amino, $C_1$-$C_{20}$-alkanoylamino, phenyl-($C_1$-$C_{20}$-alkyl)-amino, cyano, carbamoyl, N-mono-($C_1$-$C_{20}$-alkyl)-carbamoyl, N,N-di-($C_1$-$C_{20}$-alkyl) carbamoyl, $C_1$-$C_{20}$-alkanoyl-carbamoyl, phenyl-$C_1$-$C_{20}$-alkyl)-carbamoyl, sulfamoyl, N-mono-($C_1$-$C_{20}$-alkyl)-sulfamoyl, N,N-di-($C_1$-$C_{20}$-alkyl)sulfamoyl, $C_1$-$C_{20}$-alkanoyl-sulfamoyl, phenyl-$C_1$-$C_{20}$-alkyl)-sulfamoyl;

and each of n and p is 0 to 4 and m is 0 to 2, with the proviso that the sum of m, n and p is at least 2;

or the bis(substituted ethynyl) compound is a compound selected from those of the formulae V or VI

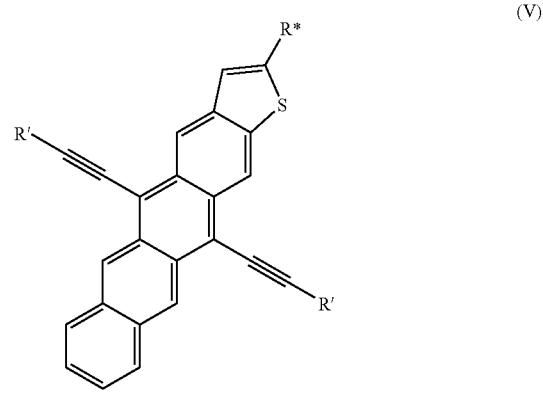

(V)

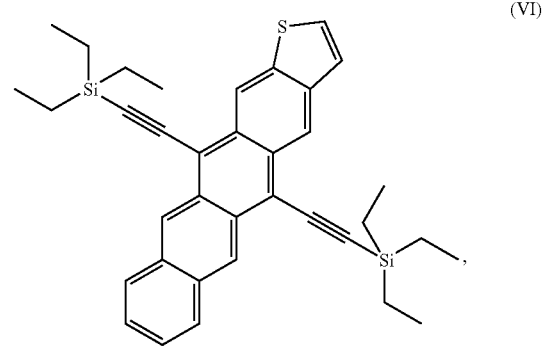

(VI)

or is a compound of the formula I* or I**,

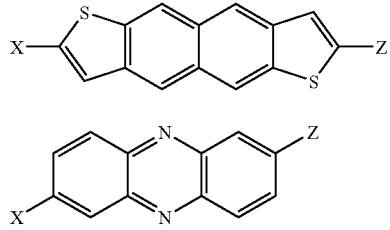

wherein each R' independently is selected from $C_1$-$C_{20}$ alkyl, benzyl, $C_1$-$C_{12}$perfluoroalkyl, $C_1$-$C_{12}$perfluoroalkanoyl, fluorophenyl, and $SiR_3$, where R independently is $C_1$-$C_6$alkoxy;

R* is hydrogen or R'; and

X and Z are substituted ethynyl as defined above.

2. A semiconductor device according to claim 1, wherein the compound of the formula I is one of the formula IA,

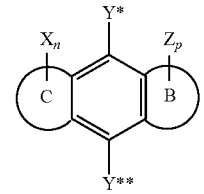

(IA)

wherein

X, Z, and the rings marked A and B, n and p are as defined for a compound of the formula I and Y* and Y are independently selected from substituted ethynyl as defined in claim 1, wherein compounds fulfil the point group and ring binding criteria given in claim 1** for compounds of the formula I.

3. A semiconductor device according to claim 2, wherein each Y in the compound of formula I, or Y* and Y** in the compound of formula IA, independently of the other, is selected from moieties given in the following table,

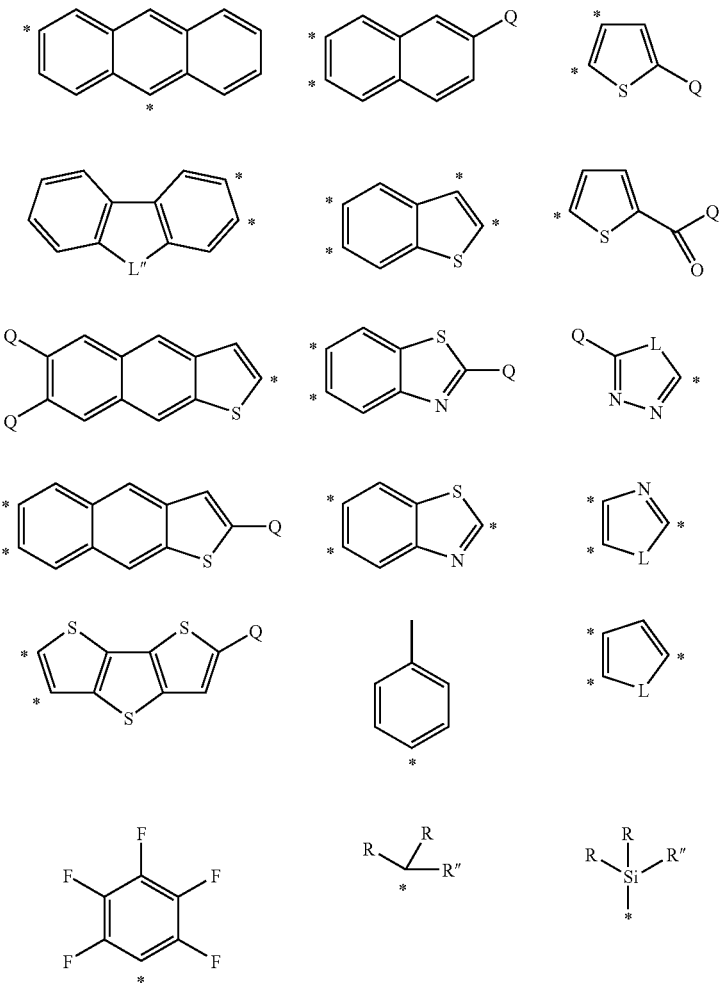

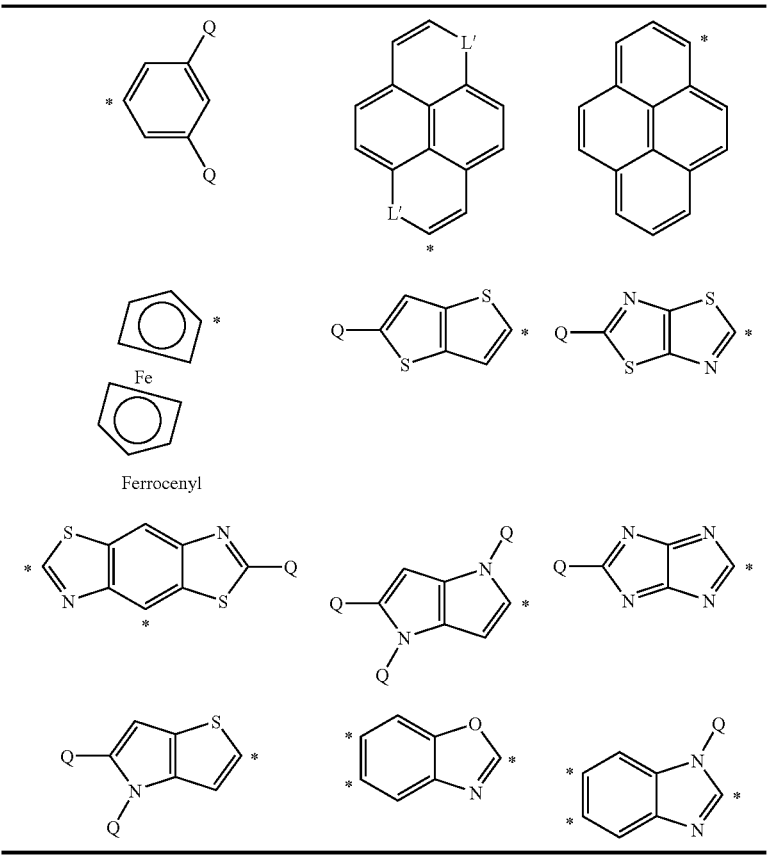

where the asterisks mark the atoms by one of which the respective moiety is bound to the ethynyl moiety and Q is as defined in claim 1;
L is O, S, NQ;
L' is O or S;
L" is O, S, NQ, $CQ_2$, $SiQ_2$;
R independently is $C_1$-$C_6$alkyl;
R" independently is H or $C_1$-$C_6$alkyl;
where the substituents of phenyl, naphthyl, anthracenyl or the heteroaryl moieties given in the preceding table are selected from the group consisting of substituted silyl[#] as defined below, formyl, $C_1$-$C_{20}$-alkyl[#], $C_2$-$C_{20}$-alkenyl[#], $C_2$-$C_{20}$-alkinyl[#], $C_6$-$C_{12}$-aryl[#], $C_6$-$C_{12}$-aryl-$C_1$-$C_{20}$-alkyl[#], heteroaryl with 5 to 14 ring atoms[#], heteroaryl-$C_1$-$C_{20}$-alkyl[#] wherein heteroaryl has 5 to 14 ring atoms, halo-$C_1$-$C_{20}$-alkyl[#], perfluorinated $C_1$-$C_{20}$-alkyl, $C_1$-$C_{20}$-alkanoyl[#], halo-$C_1$-$C_{20}$-alkylcarbonyl, halo, hydroxy, $C_1$-$C_{20}$-alkoxy, $C_3$-$C_{20}$-alkenyloxy, $C_3$-$C_{20}$-alkynyloxy, $C_1$-$C_{20}$-alkthio, $C_3$-$C_{20}$-alkenylthio, $C_3$-$C_{20}$-alkynylthio, carboxy, $C_1$-$C_{20}$-alkoxy-carbonyl[#], phenyl-$C_1$-$C_{20}$-alkoxy-carbonyl[#]), amino, N-mono- or N,N-di-($C_1$-$C_{20}$-alkyl, $C_1$-$C_{20}$-alkanoyl and/or phenyl-$C_1$-$C_{20}$-alkyl)-amino, cyano, carbamoyl, N-mono- or N,N-di-($C_1$-$C_{20}$-alkyl, $C_1$-$C_{20}$-alkanoyl and/or phenyl-$C_1$-$C_7$-alkyl)-carbamoyl, nitro and sulfamoyl, where the substituents marked with a double cross ([#]) can also be bound to a nitrogen instead of an H;
substituted silyl where mentioned is silyl substituted by two or three moieties selected from $C_1$-$C_{20}$-alkyl, $C_1$-$C_{20}$alkoxy, and phenyl- or naphthyl-$C_1$-$C_{20}$-alkyl;
X, Z, Z* and Z**, if present, are independently of each other selected from the group consisting of unsubstituted or substituted $C_1$-$C_{20}$-alkyl, halogen substituted-$C_1$-$C_{20}$-alkyl, unsubstituted or substituted $C_2$-$C_{20}$-alkenyl, unsubstituted or substituted $C_2$-$C_{20}$-alkynyl, unsubstituted or substituted $C_6$-$C_{14}$-aryl, unsubstituted or substituted heteroaryl with 5 to 14 ring atoms, unsubstituted or substituted $C_6$-$C_{14}$-aryl-$C_1$-$C_{20}$-alkyl, unsubstituted or substituted heteroaryl-$C_1$-$C_{20}$-alkyl, wherein the heteroaryl has 5 to 14 ring atoms, unsubstituted or substituted ferrocenyl, unsubstituted or substituted $C_1$-$C_{20}$-alkanoyl, perfluorinated $C_2$-$C_{10}$-alkanoyl, halo, unsubstituted or substituted $C_1$-$C_{20}$-alkoxy, $C_3$-$C_{20}$-alkenyloxy, $C_3$-$C_{20}$-alkynyloxy, unsubstituted or substituted $C_1$-$C_{20}$-alkylthio, $C_3$-$C_{20}$-alkenylthio, $C_3$-$C_{20}$-alkynylthio, carboxy, unsubstituted or substituted $C_1$-$C_{20}$-alkoxy-carbonyl, unsubstituted or substituted phenyl-$C_1$-$C_{20}$-alkoxy-carbonyl, amino, N-mono- or N,N-di-($C_1$-$C_{20}$-alkyl, $C_1$-$C_{20}$-alkanoyl and/or phenyl-$C_1$-$C_{20}$-alkyl)-amino, cyano, carbamoyl, N-mono- or N,N-di-($C_1$-$C_{20}$-alkyl, $C_1$-$C_{20}$-alkanoyl and/or phenyl-$C_1$-$C_{20}$-alkyl)-carbamoyl and sulfamoyl, where in each case where substituted forms are mentioned, the substitutents are selected from those mentioned above as substituents for phenyl, naphthyl, anthracenyl or heteroaryl;
and each of n and p is 0 to 2.

4. A semiconductor device according to claim 3 wherein in the compound of the formula I or IA each of the rings B and C is optionally substituted and is a ring selected from the following moieties where the dotted bonds marks the side of the ring or ring system annealed to the central ring A in formula I or IA:

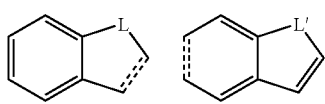

L = S, NQ, O;   L' = NQ, O

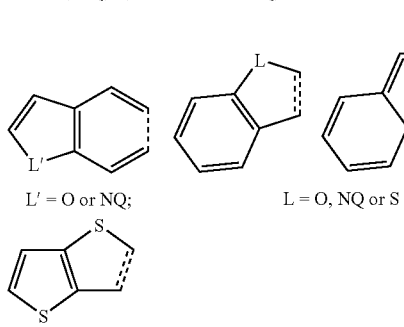

L' = O or NQ;   L = O, NQ or S

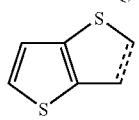

or one of rings B or C is selected from the preceding moieties, and the other is of the formula

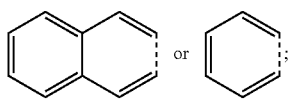

Q is, for each occurrence of Q and each ring independently of the other, hydrogen, $C_1$-$C_{20}$-alkyl, phenyl-$C_1$-$C_{20}$-alkyl, $C_1$-$C_{20}$-alkylphenyl-$C_1$-$C_{20}$-alkyl, or halo-$C_1$-$C_{20}$-alkylcarbonyl, especially perfluoro-$C_1$-$C_{20}$-alkylcarbonyl;

each Y or Y* and Y** is, independently of the other selected from substituted ethynyl wherein the substituents are selected from $C_1$-$C_{20}$-alkyl, unsubstituted or $C_1$-$C_{20}$-alkyl-substituted phenyl, halo-phenyl, pentafluorophenyl, naphthyl, anthracenyl, tri-($C_1$-$C_{20}$-alkyl)-silyl and a moiety selected from the moieties of the following formulae which may be unsubstituted or substituted by $C_1$-$C_{20}$-alkyl, phenyl or naphthyl:

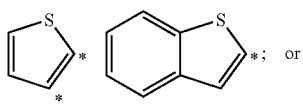

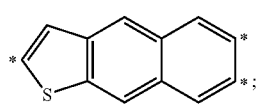

X and Z if present as optional substituents are selected from the group consisting of $C_1$-$C_{20}$-alkyl, phenyl, $C_1$-$C_{20}$-alkyl-substituted phenyl, naphthyl, phenyl- or naphthyl-$C_1$-$C_{20}$-alkyl, halo-$C_1$-$C_{20}$-alkylcarbonyl and perfluoro-$C_1$—$CH_{20}$-alkylcarbonyl;

each of n and p is, independently of the other, 0, 1 or 2 and m is 2.

5. A semiconductor device according to claim 1 or claim 2 wherein the compound of the formula I or IA is of the formula IB,

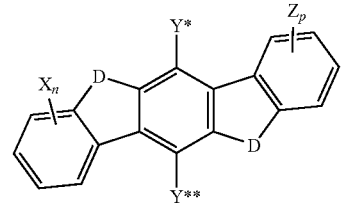

(IB)

wherein each of D is a heteroatom selected from the group consisting of NH or S or O; X, Z, n and p are as defined for a compound of the formula I or IA; and Y* and Y are independently selected from substituted ethynyl, which compounds also fulfil the point group and ring binding criteria given in claim 1** for compounds of the formula I, or of the formula IC,

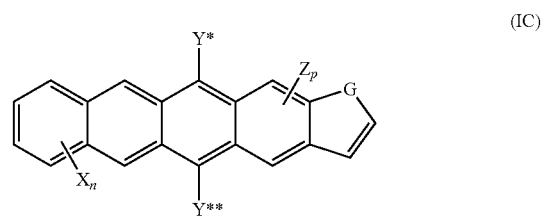

(IC)

wherein G is O or NQ; X, Z, n and p are as defined for a compound of the formula I; and Y* and Y** are independently selected from substituted ethynyl, which compounds also fulfil the point group and ring binding criteria given above for compounds of the formula I.

6. A semiconductor device according to claim 5 wherein
the compound of the formula I, formula IA or formula IB has $C_{2h}$ point symmetry.

7. A semiconductor device according to claim 1 wherein the compound of the formula I is a compound of the formula I* or I**,

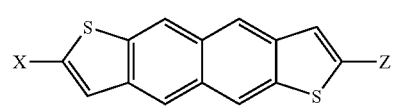

I*

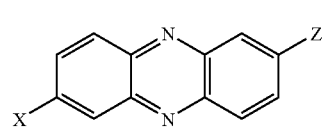

I** wherein X and Z are substituted ethynyl as defined for a compound of the formula I in claim 1 or as defined for Y as defined above.

8. A semiconductor device according to claim 1 wherein the compound of the formula I is a compound selected from those of the formulae:
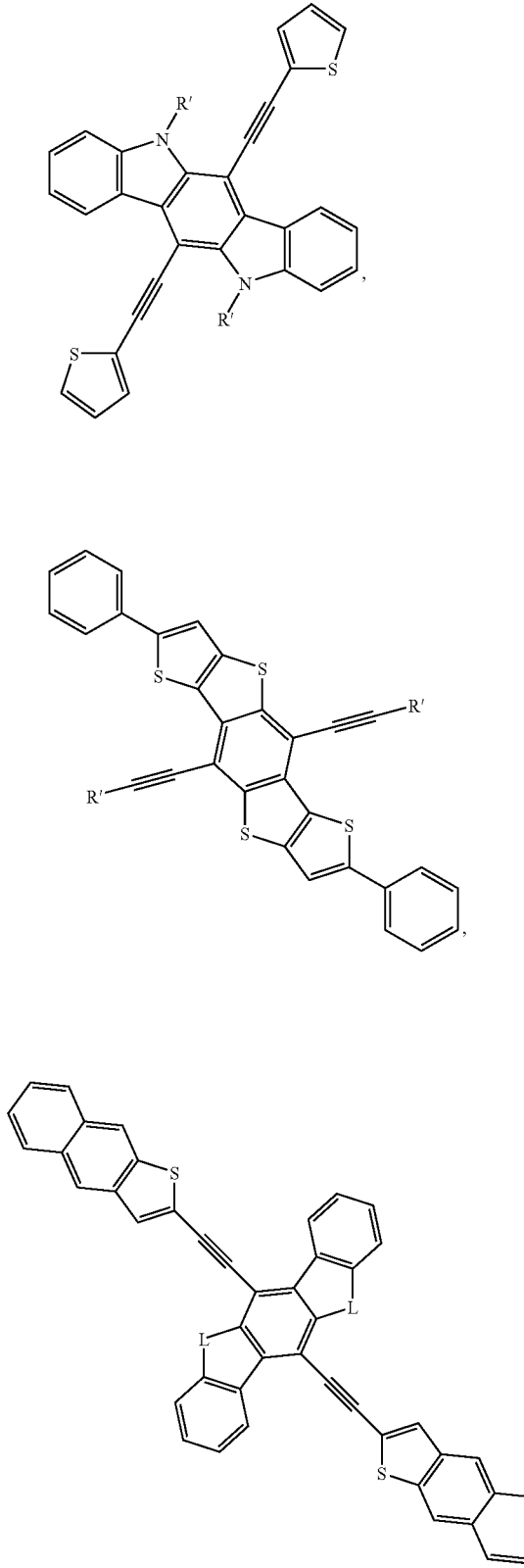
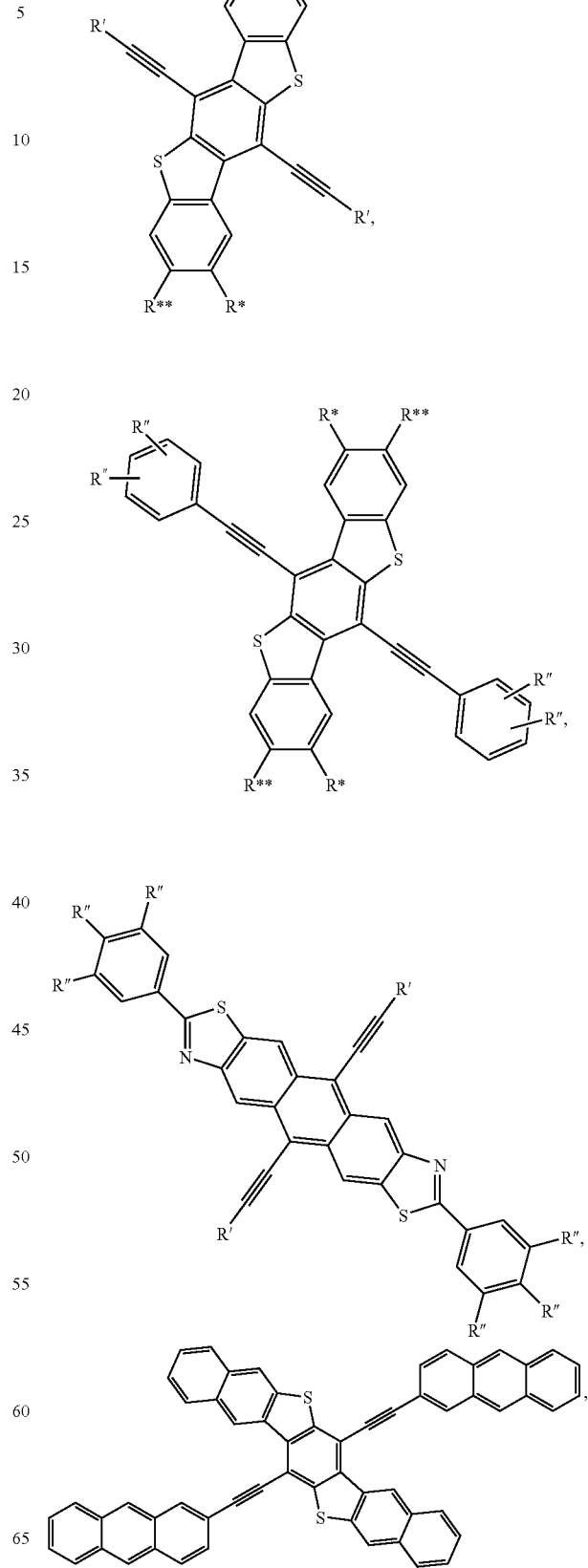

-continued

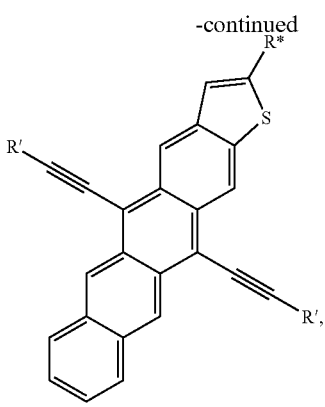

wherein each R' independently is selected from C$_1$-C$_{20}$alkyl, benzyl, C$_1$-C$_{12}$perfluoroalkyl, C$_1$-C$_{12}$perfluoroalkanoyl, fluorophenyl, and SiR$_3$, where R independently is C$_1$-C$_6$alkyl, C$_1$-C$_6$alkoxy;
R", R* and R** independently are hydrogen or R', and
L is O or S.

9. A semiconductor device according to claim 1 wherein the compound of the formula I is a compound selected from those of the formulae:

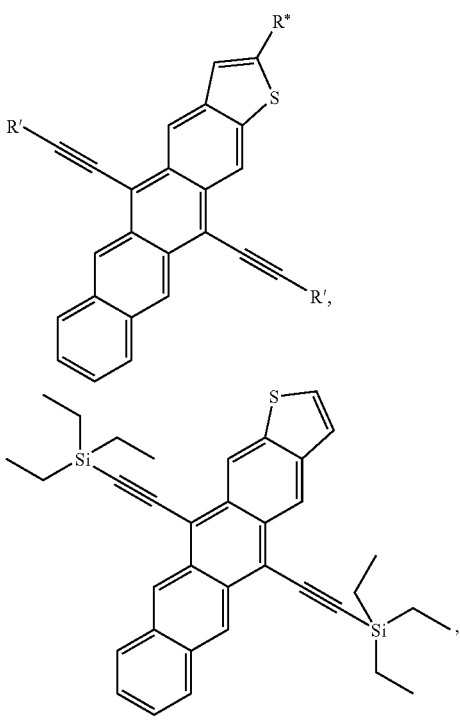

wherein each R' independently is selected from C$_1$-C$_{20}$alkyl, benzyl, C$_1$-C$_{12}$perfluoroalkyl, C$_1$-C$_{12}$perfluoroalkanoyl, fluorophenyl, and SiR$_3$, where R independently is C$_1$-C$_6$alkoxy; and
R* is hydrogen or R'.

10. A semiconductor device according to claim 1, which is a diode, an organic field effect transistor, or a device containing a diode and/or an organic field effect transistor.

11. An essentially isomerically pure compound of the formula I, I*, or I** according to claim 1 wherein the rings marked A, B and C that constitute the backbone of formula I are ortho-annealed, with the proviso that the backbone together with the ethynyl groups has a point symmetry selected from the group consisting of C$_{2h}$, D$_{2h}$ and C$_s$ point symmetry group.

12. A semiconducting layer formulation, or a semiconducting layer in a semiconductor device, characterized in that 90% by weight or more of the semiconducting material is an isomerically pure compound of the formula I, I* or I** as defined in claim 11.

13. A process for preparing a thin film transistor device from a compound of the formula I, I*, I**, V or VI according to claim 1 comprising the steps of:
  depositing a plurality of electrically conducting gate electrodes on a substrate;
  depositing a gate insulator layer on said electrically conducting gate electrodes;
  depositing a layer of a compound of the formula I, V, I*, II*, or VI or a precursor thereof on said insulator layer such that said layer of compound of formula I, V, I*, II*, or VI substantially overlaps said gate electrodes;
  depositing a plurality of sets of electrically conductive source and drain electrodes on said layer such that each of said sets is in alignment with each of said gate electrodes; thereby producing the thin film transistor device.

14. A process according to claim 13 for the preparation of an organic thin film transistor, wherein a film of the compound of the formula I, V, I*, II*, or VI is formed having a thickness in the range of from 5 to 200 nm.

15. A semiconductor device according to claim 1 wherein the rings or ring systems marked B and C in the compound of the formula I each contain at least one heteroatom with 4 to 20 ring atoms in total.

16. A semiconductor device according to claim 15 wherein the rings or ring systems marked B and C in the compound of the formula I each contain at least one heteroatom with up to 14 ring atoms in total.

17. A semiconductor device according to claim 6 wherein the compound of the formula I or formula IA has D$_{2h}$ point symmetry.

18. A semiconductor device according to claim 17 wherein the compound of the formula I, formula IA, or formula IC has C$_s$ symmetry.

* * * * *